(12) United States Patent
Jin et al.

(10) Patent No.: US 10,188,099 B2
(45) Date of Patent: Jan. 29, 2019

(54) HIGH DENSITY CELL BANKING METHODS

(71) Applicant: Genzyme Corporation, Cambridge, MA (US)

(72) Inventors: Xiaoxia Jin, Framingham, MA (US); Haodi Dong, Framingham, MA (US); Claudia Buser, Framingham, MA (US)

(73) Assignee: GENZYME CORPORATION, Boston, MA (US)

( * ) Notice: Subject to any disclaimer, the term of this patent is extended or adjusted under 35 U.S.C. 154(b) by 0 days.

(21) Appl. No.: 14/212,607

(22) Filed: Mar. 14, 2014

(65) Prior Publication Data

US 2014/0273206 A1    Sep. 18, 2014

Related U.S. Application Data

(60) Provisional application No. 61/793,021, filed on Mar. 15, 2013.

(51) Int. Cl.

| | |
|---|---|
| C12M 1/00 | (2006.01) |
| C12N 5/00 | (2006.01) |
| A01N 1/02 | (2006.01) |
| C12M 3/06 | (2006.01) |
| C12M 1/34 | (2006.01) |

(52) U.S. Cl.
CPC ........... *A01N 1/0284* (2013.01); *C12M 23/26* (2013.01); *C12M 27/16* (2013.01); *C12M 29/10* (2013.01); *C12M 29/16* (2013.01); *C12M 41/46* (2013.01); *C12M 45/22* (2013.01)

(58) Field of Classification Search
None
See application file for complete search history.

(56) References Cited

U.S. PATENT DOCUMENTS

| | | | |
|---|---|---|---|
| 6,100,061 | A | 8/2000 | Reiter et al. |
| 6,475,725 | B1 | 11/2002 | Reiter et al. |
| 6,544,424 | B1 | 4/2003 | Shevitz |
| 6,544,788 | B2 | 4/2003 | Singh |
| 8,084,252 | B2 | 12/2011 | Reiter et al. |
| 8,153,425 | B2 * | 4/2012 | Pogue-Caley et al. ....... 435/372 |
| 2003/0054331 | A1 | 3/2003 | Fraser et al. |
| 2006/0166364 | A1 * | 7/2006 | Senesac .................. 435/456 |
| 2014/0011270 | A1 * | 1/2014 | Chotteau et al. ............ 435/326 |
| 2016/0100570 | A1 | 4/2016 | Jin et al. |

FOREIGN PATENT DOCUMENTS

| | | | |
|---|---|---|---|
| EP | 2308958 A2 | 4/2011 | |
| WO | 1996026266 A1 | 8/1996 | |
| WO | 1997005240 A1 | 2/1997 | |
| WO | 2000011102 A1 | 3/2000 | |
| WO | 2001038362 A2 | 5/2001 | |
| WO | WO2011/091248 A1 * | 7/2011 | ............. B01D 63/02 |
| WO | 2011140241 A2 | 11/2011 | |
| WO | 2013006461 A1 | 1/2013 | |
| WO | 2014/143691 A1 | 9/2014 | |

OTHER PUBLICATIONS

Seth, G. et al. 2013. Development of a new bioprocess scheme using frozen seed train intermediates to initiate CHO cell culture manufacturing campaigns. Biotechnology and Bioengineering 110: 1376-1385. specif. pp. 1377, 1378, 1381.*
Woods, E.J. et al. 2010. Container system for enabling commercial production of cryopreserved cell therapy products. Regenerative Medicine 5(4): 659-667. specif. pp. 659, 660, 661.*
Spectrum Laboratories, Inc. Hollow fiber filters. Datasheet [online]. Spectrumlabs.com, Copyright 1995-2015 [retrieved on Jun. 12, 2015]. Retrieved from the Internet: <URL: http://www.spectrumlabs.com/filtration/mPESKrosFloList.html>.*
Nieminen, A. et al. 2011. The use of the ATF system to culture Chinese hamster ovary cells in a concentrated fed-batch system. BioPharm International 24(6): 1-6. specif. pp. 1-6.*
Chotteau, V. et al. 2010. Study of alternating tangential flow filtration for perfusion and harvest in Chinese hamster ovary cells cultivation. Digitala Vetenskapliga Arkivet (DiVA), Abstract, pp. 1-2. Retrieved from the internet: http://www.diva-portal.org/smash/record.jsf?pid=diva2%3A501617&dswid=7622.*
Logan et al. Adenovirus Tripartite Leader Sequence Enhances Translation of mRNAs Late after Injection. PNAS. 1984, vol. 81, pp. 3655-3659.
Bitter et al. 'Expression and secretion vectors for yeast'. Methods in Enzymology. 1987, vol. 153, pp. 516-544.
International Search Report and Written Opinion of the International Searching Authority for International application No. PCT/US2014/027757, dated Aug. 20, 2014 (15 pages).
Clincke et al. (May 1, 2013) "Very High Density of CHO Cells in Perfusion by ATF or TFF in WAVE Bioreactor™. Part I. Effect of the Cell Density on the Process," Biotechnology Progress. 29(3):754-767.
Clincke et al. (May 21, 2013) "Very High Density of Chinese Hamster Ovary Cells in Perfusion by Alternating Tangential Flow or Tangential Flow Filtration in WAVE Bioreactor™—Part II: Applications for Antibody Production and Cryopreservation," Biotechnology Progress. 29(3):768-777.
Ninomiya et al. (1991) "Large-scale, high-density freezing of hybridomas and its application to high-density culture," Biotechnol. Bioeng. 38:1110-1113.
Ozturk (1996) "Engineering challenges in high density cell culture systems," Cytotechnology. 22:3-16.
Singh (1999) "Disposable bioreactor for cell culture using wave-induced agitation," Cytotechnology. 30:149-158.

(Continued)

*Primary Examiner* — Renee Claytor
*Assistant Examiner* — Sharon M. Papciak
(74) *Attorney, Agent, or Firm* — Lathrop Gage LLP; James H. Velema, Esq.

(57) ABSTRACT

The current disclosure provides a method for the creation of a high-density cryopreserved cell bank using perfusion culture techniques and non-centrifugal concentration of cells. Methods of production using this high-density cryopreserved cell bank are also provided.

30 Claims, 11 Drawing Sheets

(56) References Cited

OTHER PUBLICATIONS

Tao et al. (Apr. 27, 2011) "Development and implementation of a perfusion-based high cell density cell banking process," Biotechnology Progress. 27(3):824-829.
International Search Report with Written Opinion corresponding to International Patent Application No. PCT/US2015/050817, dated Nov. 27, 2015.
Heidemann et al. (2010) "Characterization of cell-banking parameters for the cryopreservation of mammalian cell lines in 100-mL cryobags," Biotechnol. Progress. 26(4):1154-1163.

* cited by examiner

A.

B.

A.

B.

A.

B.

A.

B.

HIGH DENSITY CELL BANKING METHODS

RELATED APPLICATIONS

This application claims priority to U.S. Provisional Application No. 61/793,021, filed Mar. 15, 2013, the contents of which are incorporated herein by reference in their entirety for all purposes.

BACKGROUND

Conventional cell banking is widely used to maintain stocks of frozen, characterized cells that may be thawed for use in a number of applications, including the production of therapeutically relevant proteins. Typically, cryopreserved stocks are maintained at lower densities or are centrifuged to create higher density aliquots for storage. Lower density stocks do not allow for efficient inoculation of large volume cultures, while centrifugation-based concentration methods can be very damaging to cells (which will become even more fragile during the cryopreservation process). Accordingly, there is a need for improved cell banking methods.

SUMMARY

The current disclosure provides improved methods for the creation of a cell bank. In certain aspects, the cell banking process of the invention employs perfusion culture techniques and non-centrifugal concentration of cells to allow for cryopreservation at unexpectedly high cell densities while retaining excellent cell viability for later use in production cell culture.

Accordingly, in one aspect, the invention provides a non-centrifugal method for producing a high-density frozen cell bank, the method comprising: a) culturing cells in a perfusion bioreactor, wherein said bioreactor is coupled to a cell retention system; b) non-centrifugally concentrating said cells to produce a concentrated cell population; and c) cryopreserving the concentrated cell population to produce a high-density frozen cell bank.

In one embodiment, the cell retention system comprises an alternating tangential flow filtration system comprising a filter. In another embodiment, the filter has a surface area of at least 0.3 $m^2$. In another embodiment, the filter has a surface area of about 0.5 to about 1.0 $m^2$. In another embodiment, the filter has a surface area of about 0.7 to about 0.8 $m^2$. In another embodiment, the filter has a surface area of about 2.0 to about 3.0 $m^2$. In another embodiment, the filter has a surface area of about 4 to about 5 $m^2$.

In one embodiment, the filter has a pore size of about 0.2 μm.

In one embodiment, the concentrated cell population has a cell density of at least about 1 ×$10^8$ cells/mL.

In one embodiment, the concentrated cell population has a cell density of about 1×$10^8$ cells/mL.

In one embodiment, the cryopreserving comprises adding DMSO to the concentrated cell population at a final concentration of about 5% to about 10%, vol/vol. In another embodiment, the cryopreserving comprises freezing at least a portion of the concentrated cell population in a container appropriate for storage under cryopreservation conditions.

In one embodiment, the container is a vial. In one embodiment, the container has a volume of at least 2 mL. In one embodiment, the container has a volume of about 5 mL.

In one embodiment, the high-density frozen cell bank comprises about 4.5×$10^8$ cells.

In one embodiment, the container is a cryobag. In another embodiment, cryobag has a volume of about 5 to about 150 mL.

In one embodiment, the high-density frozen cell bank has a cell density of about 1×$10^8$ cells/mL.

In one embodiment, the perfusion rate in the perfusion bioreactor is at least about 0.2 nL/cell/day.

In one embodiment, the perfusion bioreactor cell culture has a pH of about 7 and a dissolved oxygen concentration of at least about 40%.

In one embodiment, the bioreactor is a flexible bag bioreactor. In another embodiment, the flexible bag bioreactor has a volume of 10 L. In another embodiment, the flexible bag bioreactor has a volume of at least 20 L. In another embodiment, the flexible bag bioreactor further comprises at least one dip tube.

In one embodiment, the high-density frozen cell bank has a post-thaw viability of at least 60%. In another embodiment, the high-density frozen cell bank has a post-thaw viability of at least 90%. In another embodiment, the high-density frozen cell bank has a post-thaw viability of at least 95%.

In one embodiment, the cells are mammalian cells. In another embodiment, the mammalian cells are selected from the group consisting of: CHO, CHO-DBX11, CHO-DG44, CHO-S, CHO-K1, Vero, BHK, HeLa, COS, MDCK, HEK-293, NIH-3T3, W138, BT483, Hs578T, HTB2, BT20, T47D, NSO, CRL7030, HsS78Bst cells, PER.C6, SP2/0-Ag14, and hybridoma cells.

In one embodiment, the cells are transfected cells.

In one aspect, the invention provides a non-centrifugal method for producing a high-density frozen cell bank, the method comprising: a) culturing cells in a perfusion bioreactor coupled to an alternating tangential flow filtration system, wherein the bioreactor comprises a flexible bag bioreactor, and wherein the filter has a filter surface area of at least 0.3 $m^2$ and a filter with a MWCO size of at least 50 kDa; b) non-centrifugally concentrating the cells using the alternating tangential flow filtration system to produce a concentrated cell population having a density of about 1×$10^8$ cells/mL; c) cryopreserving the concentrated cell population to produce a high-density frozen cell bank, wherein the cryopreserving comprises adding DMSO to the concentrated cell population to a final concentration of about 5% to about 10%, vol/vol; and wherein the high-density frozen cell bank has a cell density of about $10^8$ cells/mL.

In one embodiment, the pH and DO of the culture are controlled by automated methods.

In one embodiment, the pH and DO of the culture are controlled by non-automated methods. In another embodiment, the pH and DO are controlled through any one or more of the following: adjustment of the mixture of gases that are introduced to the culture, adjustment of the rock rate of the bioreactor, or adjustment of the rock angle of the bioreactor.

In one embodiment, the bioreactor is rocked at 15 rpm with a rock angle of 8°.

Accordingly, in one aspect, the invention provides a non-centrifugal method for producing a high-density frozen cell bank, the method comprising: a) culturing cells in a perfusion bioreactor, wherein said bioreactor is coupled to a cell retention system; b) non-centrifugally concentrating said cells to produce a concentrated cell population; and c) cryopreserving the concentrated cell population to produce a high-density frozen cell bank.

In one embodiment, the cell retention system comprises an alternating tangential flow filtration system comprising a filter. In another embodiment, the filter has a surface area of at least 0.3 m². In another embodiment, the filter has a surface area of about 0.5 to about 1.0 m². In another embodiment, the filter has a surface area of about 0.7 to about 0.8 m². In another embodiment, the filter has a surface area of about 2.0 to about 3.0 m². In another embodiment, the filter has a surface area of about 4 to about 5 m².

In one embodiment, the filter has a pore size of about 0.2 µm.

In one embodiment, the concentrated cell population has a cell density of at least about 1.1×10^8 cells/mL.

In one embodiment, the concentrated cell population has a cell density of about 1.1×10^8 cells/mL.

In one embodiment, the cryopreserving comprises adding DMSO to the concentrated cell population at a final concentration of about 5% to about 10%, vol/vol. In another embodiment, the cryopreserving comprises freezing at least a portion of the concentrated cell population in a container appropriate for storage under cryopreservation conditions.

In one embodiment, the container is a vial. In one embodiment, the container has a volume of at least 2 mL. In one embodiment, the container has a volume of about 5 mL.

In one embodiment, the high-density frozen cell bank comprises about 4.5×10^8 cells.

In one embodiment, the container is a cryobag. In another embodiment, cryobag has a volume of about 5 to about 150 mL.

In one embodiment, the high-density frozen cell bank has a cell density of about 1×10^8 cells/mL.

In one embodiment, the perfusion rate in the perfusion bioreactor is at least about 0.2 nL/cell/day.

In one embodiment, the perfusion bioreactor cell culture has a pH of about 7 and a dissolved oxygen concentration of at least about 40%.

In one embodiment, the bioreactor is a flexible bag bioreactor. In another embodiment, the flexible bag bioreactor has a volume of 10 L. In another embodiment, the flexible bag bioreactor has a volume of at least 20 L. In another embodiment, the flexible bag bioreactor further comprises at least one dip tube.

In one embodiment, the high-density frozen cell bank has a post-thaw viability of at least 60%. In another embodiment, the high-density frozen cell bank has a post-thaw viability of at least 90%. In another embodiment, the high-density frozen cell bank has a post-thaw viability of at least 95%.

In one embodiment, the cells are mammalian cells. In another embodiment, the mammalian cells are selected from the group consisting of: CHO, CHO-DBX11, CHO-DG44, CHO-S, CHO-K1, Vero, BHK, HeLa, COS, MDCK, HEK-293, NIH-3T3, W138, BT483, Hs578T, HTB2, BT20, T47D, NSO, CRL7030, HsS78Bst cells, PER.C6, SP2/0-Ag14, and hybridoma cells.

In one embodiment, the cells are transfected cells.

In one aspect, the invention provides a non-centrifugal method for producing a high-density frozen cell bank, the method comprising: a) culturing cells in a perfusion bioreactor coupled to an alternating tangential flow filtration system, wherein the bioreactor comprises a flexible bag bioreactor, and wherein the filter has a filter surface area of at least 0.3 m² and a filter with a MWCO size of at least 50 kDa; b) non-centrifugally concentrating the cells using the alternating tangential flow filtration system to produce a concentrated cell population having a density of about 1.1×10^8 cells/mL; c) cryopreserving the concentrated cell population to produce a high-density frozen cell bank, wherein the cryopreserving comprises adding DMSO to the concentrated cell population to a final concentration of about 5% to about 10%, vol/vol; and wherein the high-density frozen cell bank has a cell density of about 10^8 cells/mL.

In one embodiment, the pH and DO of the culture are controlled by automated methods.

In one embodiment, the pH and DO of the culture are controlled by non-automated methods. In another embodiment, the pH and DO are controlled through any one or more of the following: adjustment of the mixture of gases that are introduced to the culture, adjustment of the rock rate of the bioreactor, or adjustment of the rock angle of the bioreactor.

In one embodiment, the bioreactor is rocked at 15 rpm with a rock angle of 8°.

In one aspect, the invention provides a non-centrifugal method for producing a high-density frozen cell bank, the method comprising: a) culturing cells in a perfusion bioreactor, wherein said bioreactor is agitated for efficient mixing and gas exchange, wherein said bioreactor is coupled to a cell retention system; b) non-centrifugally concentrating said cells to produce a concentrated cell population; and c) cryopreserving the concentrated cell population to produce a high-density frozen cell bank.

In one embodiment, the cell retention system comprises an alternating tangential flow filtration system comprising a filter. In another embodiment, the filter has a surface area of at least 0.3 m². In another embodiment, the filter has a surface area of about 0.5 to about 1.0 m². In another embodiment, the filter has a surface area of about 0.7 to about 0.8 m². In another embodiment, the filter has a surface area of about 2.0 to about 3.0 m². In another embodiment, the filter has a surface area of about 4 to about 5 m².

In one embodiment, the filter has a pore size selected from the group consisting of 0.2 µm, 0.4 µm, and 0.65 µm.

In one embodiment, the concentrated cell population has a cell density selected from the group consisting of 1.0×10^8 cells/mL, 1.1×10^8 cells/mL, 1.2×10^8 cells/mL, 1.3×10^8 cells/mL, 1.5×10^8 cells/mL, 1.7×10^8 cells/mL, and 2.0×10^8 cells/mL.

In one embodiment, the cryopreserving comprises adding DMSO to the concentrated cell population at a final concentration of about 5% to about 10%, vol/vol. In another embodiment, the cryopreserving comprises freezing at least a portion of the concentrated cell population in a container appropriate for storage under cryopreservation conditions.

In one embodiment, the container is a vial. In one embodiment, the container has a volume of at least 2 mL. In one embodiment, the container has a volume of about 5 mL.

In one embodiment, the high-density frozen cell bank comprises about 4.5×10^8 cells.

In one embodiment, the container is a cryobag. In another embodiment, cryobag has a volume of about 5 to about 150 mL.

In one embodiment, the high-density frozen cell bank has a cell density of about 1×10^8 cells/mL.

In one embodiment, the perfusion rate in the perfusion bioreactor is between about 0.02 nL/cell/day to about 0.5 nL/cell/day.

In one embodiment, the perfusion bioreactor cell culture has a pH of between about 6.8 and about 7.2.

In one embodiment, the perfusion bioreactor cell culture has a dissolved oxygen concentration of at least about 30%.

In one embodiment, the bioreactor is a flexible bag bioreactor. In another embodiment, the flexible bag bioreactor has a volume of 10 L. In another embodiment, the flexible bag bioreactor has a volume of at least 20 L. In another embodiment, the flexible bag bioreactor further comprises at least one dip tube.

In one embodiment, the high-density frozen cell bank has a post-thaw viability of at least 60%. In another embodiment, the high-density frozen cell bank has a post-thaw viability of at least 90%. In another embodiment, the high-density frozen cell bank has a post-thaw viability of at least 95%.

In one embodiment, the cells are mammalian cells. In another embodiment, the mammalian cells are selected from the group consisting of: CHO, CHO-DBX11, CHO-DG44, CHO-S, CHO-K1, Vero, BHK, HeLa, COS, MDCK, HEK-293, NIH-3T3, W138, BT483, Hs578T, HTB2, BT20, T47D, NSO, CRL7030, HsS78Bst cells, PER.C6, SP2/0-Ag14, and hybridoma cells.

In one embodiment, the cells are transfected cells.

In one aspect, the invention provides a non-centrifugal method for producing a high-density frozen cell bank, the method comprising: a) culturing cells in a perfusion bioreactor coupled to an alternating tangential flow filtration system, wherein the bioreactor comprises a flexible bag bioreactor, and wherein the filter has a filter surface area of at least 0.3 m$^2$ and a filter with a MWCO size of at least 50 kDa; b) non-centrifugally concentrating the cells using the alternating tangential flow filtration system to produce a concentrated cell population having a density of greater than about $1.0 \times 10^{\wedge}8$ cells/mL; c) cryopreserving the concentrated cell population to produce a high-density frozen cell bank, wherein the cryopreserving comprises adding DMSO to the concentrated cell population to a final concentration of about 5% to about10%, vol/vol; and wherein the high-density frozen cell bank has a cell density of about $10^{\wedge}8$ cells.

In one embodiment, the pH and DO of the culture are controlled by automated methods.

In one embodiment, the pH and DO of the culture are controlled by non-automated methods. In another embodiment, the pH and DO are controlled through any one or more of the following: adjustment of the mixture of gases that are introduced to the culture, adjustment of the rock rate of the bioreactor, or adjustment of the rock angle of the bioreactor.

In one embodiment, the bioreactor is rocked at least at a rate of 15 rpm with at least a rock angle of 8°.

In one embodiment, the bioreactor is rocked at a rate of 15 rpm with a rock angle of 8°.

In one embodiment, the bioreactor is rocked at 22 rpm with a rock angle of 10°.

DETAILED DESCRIPTION

Figure 1:
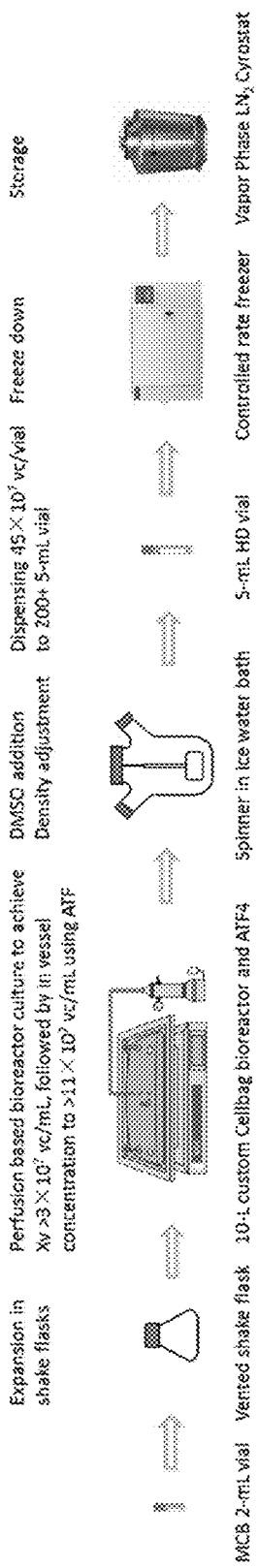
FIG. 1: is a drawing of a high density cell cryobanking process.

The current disclosure provides a method of high-density cell cryobanking that comprises the use of a perfusion culture system linked to a non-centrifugal cell retention device.

I. Definitions

As used herein, the term "batch culture" refers to a cell culturing technique in which a quantity of fresh culture medium is inoculated with cells that rapidly enter a logarithmic growth phase and in which the growth medium of the culture is not continuously removed and replaced with fresh medium.

As used herein, the term "fed batch culture" refers to a cell culturing technique in which a quantity of fresh culture medium is inoculated with cells initially, and additional culture nutrients are fed (continuously or in discrete increments) to the culture during the culturing process, with or without periodic cell and/or product harvest before termination of culture.

As used herein, the term "perfusion culture" refers to a cell culturing technique in which a quantity of fresh medium is inoculated with cells that rapidly enter a logarithmic growth phase (as above) and in which the growth medium is continuously removed from a culture and replaced with fresh medium.

As used herein, the term "bioreactor" shall refer to a vessel for culturing cells.

In one embodiment, the bioreactor is a "flexible bag bioreactor". A "flexible bag bioreactor" is a sterile chamber capable of receiving a liquid media and which additionally comprises connectors, ports, adaptors and flexible tubing. In one embodiment, the chamber is made of plastic. In a specific embodiment, the chamber is made of multilayered laminated clear plastic. In a further specific embodiment, the chamber is made of multilayer laminated clear plastic and has a fluid contact layer made of USP Class VI ethylene vinyl acetate/low density polyethylene copolymer while the outer layer is made of low density polyethylene.

Additionally, the connectors, ports, and adaptors may be made from any kind of plastic including but not limited to: polyethylene, polypropylene, and polycarbonate while the tubing may be constructed from any kind of plastic including but not limited to: thermoplastic elastomer or silicone (e.g. platinum-cured silicone).

Appropriate "flexible bag bioreactor" chambers can be commonly found in the art and include, but are not limited to, those described in U.S. Pat. No. 6,544,788, which is herebyincorporated by reference in its entirety.

The "flexible bag bioreactor" chamber can be partially filled with culture media and then inflated to rigidity. It may then be placed on a rocking platform (such as a BASE20/50EHT rocking unit from GE Healthcare Life Sciences) that moves back and forth through a preset rocking angle and preset rocking rate. This rocking motion induces wave-like motions in the culture media, promoting agitation and oxygen transfer in order to improve the performance of the cell culture. The preset rocking angle may be at least about 4 degrees, e.g. about 4 degrees, 5 degrees, 6 degrees, 7 degrees, 8 degrees, 9 degrees, 10 degrees, 11 degrees, or 12 degrees. Furthermore, the preset rocking rate may be set at rock rate per minute (rpm) that is at least about 6 rpm, e.g. about 7 rpm, 8 rpm, 9 rpm, 10 rpm, 11 rpm, 12 rpm, 13 rpm, 14 rpm, 15 rpm, 16 rpm, 17 rpm, 18 rpm, 19 rpm, 20 rpm, 21 rpm, 22 rpm, 23 rpm, 24 rpm, 25 rpm, 26 rpm, 27 rpm, 28 rpm, 29 rpm, 30 rpm, 31 rpm, 32 rpm, 33 rpm, 34 rpm, 35 rpm, 36 rpm, 37 rpm, 38 rpm, 39 rpm, or 40 rpm. In a specific embodiment, the rock rate per minute is about 8 rpm. In a specific embodiment, the rock rate per minute is about 15 rpm. In another specific embodiment, the rock rate per minute is about 22 rpm.

As used herein, the term "cell retention system" refers to all devices with the ability to separate cells from medium and the waste products therein by the use of a filter. Filters may include membrane, ceramic, or metal filters in any shape including spiral wound, tubular, or sheet. Filters may be of different surface areas. For example, the filter surface area may be about 0.3 $m^2$ to about 5 $m^2$, e.g. about 0.3 $m^2$, 0.4 $m^2$, 0.5 $m^2$, 0.6 $m^2$, 0.7 $m^2$, 0.77 $m^2$, 0.8 $m^2$, 0.9 $m^2$, 1.0 $m^2$, 1.1 $m^2$, 1.2 $m^2$, 1.3 $m^2$, 1.4 $m^2$, 1.5 $m^2$, 1.6 $m^2$, 1.7 $m^2$, 1.8 $m^2$, 1.9 $m^2$, 2.0 $m^2$, 2.1 $m^2$, 2.2 $m^2$, 2.3 $m^2$, 2.4 $m^2$, 2.5 $m^2$, 2.6 $m^2$, 2.7 $m^2$, 2.8 $m^2$, 2.9 $m^2$, 3.0 $m^2$, 3.1 $m^2$, 3.2 $m^2$, 3.3 $m^2$, 3.4 $m^2$, 3.5 $m^2$, 3.6 $m^2$, 3.7 $m^2$, 3.8 $m^2$, 3.9 $m^2$, 4.0 $m^2$, 4.1 $m^2$, 4.2 $m^2$, 4.3 $m^2$, 4.4 $m^2$, 4.5 $m^2$, 4.6 $m^2$, 4.7 $m^2$, 4.8 $m^2$, 4.9 $m^2$, or about 5 $m^2$. In certain embodiments, the filter module has a molecular mass cut off (MWCO) size from about 10 kilodaltons (kDa) to about 100 kDa, e.g. it is about 10 kDa, 20 kDa, 30 kDa, 40 kDa, 50 kDa, 60 kDa, 70 kDa, 80 kDa, 90 kDa, or 100 kDa. In other embodiments, the filter module has a mesh or pore size from about 0.1 μm to about 3 μm, e.g. about 0.1 μm, 0.2 μm, 0.3 μm, 0.4 μm, 0.5 μm, 0.6 μm, 0.65 μm, 0.7 μm, 0.8 μm, 0.9 μm, 1.0 μm, 1.1 μm, 1.2 μm, 1.3 μm, 1.4 μm, 1.5 μm, 1.6 μm, 1.7 μm, 1.8 μm, 1.9 μm, 2.0 μm, 2.1 μm, 2.2 μm, 2.3 μm, 2.4 μm, 2.5 μm, 2.6 μm, 2.7 μm, 2.8 μm, 2.9 μm, or about 3.0 μm.

As used herein, the term "cryopreservation" refers to a process by which cells, tissues, or any other substances susceptible to damage caused by time or by enzymatic or chemical activity are preserved by cooling and storing them to sub-zero temperatures.

As used herein, the term "cryobanking" refers to a technique by which cells are mixed with a cryoprotectant (e.g. DMSO with or without hydroxyethyl starch (HES)) and placed in a container appropriate for storage under cryopreservation conditions. These containers are then frozen using techniques well known in the art and stored at low temperatures, typically between about −130° C. and about −195° C. The collection of cells obtained by the process is a cell bank.

In one embodiment, the cell bank is a high density cell bank. As used herein, the term "high density cell bank" shall refer to cryobanked aliquots of cells that have been frozen at a high density, wherein the density is at least about $7 \times 10^7$ viable cells/mL, e.g. it is about $7 \times 10^7$ viable cells/mL, $8 \times 10^7$ viable cells/mL, $9 \times 10^7$ viable cells/mL, $1 \times 10^8$ viable cells/mL, $2 \times 10^8$ viable cells/mL, or $3 \times 10^8$ viable cells/mL. The cells may be frozen according to any method available in the art and in any container appropriate for storage under cryopreservation conditions.

In another embodiment, the cell bank is a master cell bank. As used herein, the term "master cell bank" shall refer to a culture of cells (e.g. fully characterized cells) that have been grown from a single clone, dispensed into storage containers (e.g. dispensed into the containers in a single operation), and stored under cryopreservation conditions as described above. In certain embodiments, the cells are suitable for later use in a production cell culture and a further harvest of the therapeutically relevant proteins produced thereby.

In another embodiment, the cell bank is a mini cell bank. As used herein, the term "mini-bank" shall refer to aliquots of cells that have been cryopreserved according to "cryobanking" procedures (as described above) but are composed of fewer samples than would normally be used to create a cell bank. This type of bank may be generally used to optimize the conditions being considered for the cryopreservation of a cell line before cell banks such as a "master cell bank" are created. As an example, a "mini-bank" is used to determine the optimal cell density for the high density cell banking procedure described in this disclosure.

As used herein, the term "container appropriate for storage under cryopreservation conditions" includes any container that may be used under conditions appropriate for cell storage between about −130° C. and about −195°. These containers include, but are not limited to, vials that are made of materials suitable for cryopreservation. These materials include polymers (e.g. polytetrafluoroethylene, polystyrene, polyethylene, or polypropylene). Furthermore, surface treatments may be applied to a surface of the cryopreservation vial in order to improve cryopreservation conditions (e.g. hydrophilic coatings which reduce adsorption and denaturation). In exemplary embodiments, the vial may have a volume of more than about 0.1 mL, e.g. the vial may have a volume of about 0.1 mL, about 0.5 mL, about 0.75 mL, about 1 mL, about 2 mL, about 2.5 mL, about 5 mL, about 10 mL, about 15 mL, about 20 mL, about 25 mL, or about 50 mL. The container may also be a cryobag.

As used herein, the term "cryobag" is a sterile chamber that is capable of receiving a liquid medium, is appropriate for cell storage between about −130° C. and about −195° C., and may additionally comprise connectors, ports, adaptors and flexible tubing. The cryobag may be constructed of any appropriate material including, but not limited to, polymers such as polytetrafluoroethylene, polystyrene, polyethylene, polypropylene, Fluorinated Ethylene Propylene (FEP) and ethylene vinyl acetate (EVA). Exemplary cryobags include but are not limited to: KryoSure® Cryopreservation bags, PermaLife™ Bags (OriGen Biomedical), CryoStore freezing bags, Freeze-Pak™ Bio-containers.

As used herein, the term "shake flask" shall refer to a vessel used as a culture flask in which the medium is constantly agitated during incubation.

As used herein, the term "shake flask seed train" shall refer to a method of cell expansion in which an aliquot of cells is first cultured (seeded) in a shake flask and grown therein. The cells are cultured according to their growth rate and are usually split into larger and/or multiple vessels during their growth until the biomass has reached a level sufficient to inoculate a bioreactor.

As used herein, the term "seed density" shall refer to the initial cell density at which a flask or bioreactor is inoculated.

As used herein, the term "therapeutically relevant protein" shall refer to any protein that may be used to create a treatment for a disease or disorder or to treat a disease or disorder in an animal, including mammals such as mice, rats, monkeys, apes, and humans. These proteins may include, but are not limited to, binding polypeptides such as monoclonal antibodies, Fc fusion proteins, anticoagulants, blood factors, bone morphogenetic proteins, engineered protein scaffolds, enzymes, growth factors, hormones, interferons, interleukins, and thrombolytics.

As used herein, the term "binding polypeptide" or "binding polypeptide" shall refer to a polypeptide (e.g., an antibody) that contains at least one binding site which is responsible for selectively binding to a target antigen of interest (e.g. a human antigen). Exemplary binding sites include an antibody variable domain, a ligand binding site of a receptor, or a receptor binding site of a ligand. In certain aspects, the binding polypeptides of the invention comprise multiple (e.g., two, three, four, or more) binding sites.

As used herein, the term "antibody" refers to such assemblies (e.g., intact antibody molecules, antibody fragments, or variants thereof) which have significant known specific immunoreactive activity to an antigen of interest (e.g. a tumor associated antigen). Antibodies and immunoglobulins comprise light and heavy chains, with or without an interchain covalent linkage between them. Basic immunoglobulin structures in vertebrate systems are relatively well understood.

The generic term "antibody" comprises five distinct classes of antibody that can be distinguished biochemically. All five classes of antibodies are clearly within the scope of the current disclosure, the following discussion will generally be directed to the IgG class of immunoglobulin molecules. With regard to IgG, immunoglobulins comprise two identical light chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

II. Perfusion Cell Culture

Traditional cell culture involves a "batch" culturing process. In this type of culture, a quantity of fresh medium is inoculated with cells that rapidly enter a logarithmic growth phase. As these cells grow and divide, they consume available nutrients from the medium and excrete harmful waste products. Over time, the culture will enter a stationary growth phase, and finally a decay phase. While modifications to the "batch" culture process have made it more efficient over time, the resultant modified batch culture protocols still result in rapid growth and decay cycles. Furthermore, the "batch" culture process has a limited capacity to reach the levels of cell density that are required to allow for high-density cell banking.

The "fed batch" culture process refers to a further improvement in cell culturing technique over traditional "batch" culture techniques. While this process allows for higher cell density growth, it is still limited in its capacity to allow for efficient growth of high-density cell cultures and, therefore, to efficiently generate cells for high-density cell banking.

In preferred embodiments, the invention employs a perfusion culture process. Perfusion culture is a method for growing cells in which a quantity of fresh medium is inoculated with cells that rapidly enter a logarithmic growth phase (as above) and in which the growth medium is continuously removed from a culture and replaced with fresh medium. In this way, the culture constantly receives fresh medium with high levels of nutrients, while medium containing waste products and with lower levels of nutrients is removed. This type of culturing allows for the maintenance of the logarithmic growth of cells in which at least one culture volume is exchanged per day and the cell concentrations can be much higher than those achieved in traditional or modified batch culture (an increase of between 2 to more than 10 fold). In one embodiment of the present invention, the cell specific perfusion rate (CSPR) may be between about 0.02 nL cell$^{-1}$ day$^{-1}$ and about 0.5 nL cell$^{-1}$ day$^{-1}$, e.g. it may be about 0.02 nL cell$^{-1}$ day$^{-1}$, 0.05 nL cell$^{-1}$ day$^{-1}$, 0.1 nL cell$^{-1}$ day$^{-1}$, 0.2 nL cell$^{-1}$ day$^{-1}$, 0.3 nL cell$^{-1}$ day$^{-1}$, 0.4 nL cell$^{-1}$ day$^{-1}$, or 0.5 nL cell$^{-1}$ day$^{-1}$. In a specific embodiment, perfusion culture can be carried out in a bioreactor with a minimum of one dip tube.

In certain embodiments, the pH, temperature, dissolved oxygen concentration (DO), and osmolarity of the culture may be adjusted to maximize culture health and productivity. One method of controlling the DO and pH of cultures is through an automated feedback controller. This type of automated controller operates using microprocessor-based computers to monitor and adjust the pH and DO of the culture and thereby maintain optimal conditions for cell growth. However, these automated feedback control systems are costly. Accordingly, in certain embodiments, a non-automated method of controlling these parameters may be employed. In one exemplary embodiment, any of: adjustment of the gas mixture flowing over the culture, adjustment of the WAVE® rock rate, or adjustment of the rock angle of the culture can be used to control selected parameters (e.g. pH or DO).

In one embodiment, the starting level of carbon dioxide gas is at about 10% and the starting level of oxygen gas is at about 20% with an air flow rate of about 0.2 liters per minute (lpm). If the pH is no more than about 6.9, the CO2 set point can be reduced from 10% to 5%. If the pH is still no more than about 6.9 at a later time point, the CO2 set point can be further reduced from 5% to 0%. If the pH is still no more than about 6.9, the perfusion rate can be increased. If the DO is no more than about 45%, the O2 set point should be raised from 20% to 30%. If the DO is no more than about 45% at a later time point, the O2 level should be raised from 30% to 40%, the rock speed should be increased to about 25 rpm, and the rock angle should be changed to about 12°.

In an embodiment, the rock rate of the culture may also be adjusted during the final concentration step to avoid the inclusion of air into the cell retention system.

i. Cell Culture Media

Any type of cell culture medium suitable for the culturing of cells can be used in the methods of the present invention. Guidelines for choosing an appropriate cell medium are well known in the art and are provided in, for example, Chapters 8 and 9 of Freshney, R. I. Culture of Animal Cells (a manual of basic techniques), 4th edition 2000, Wiley-Liss; and in Doyle, A., Griffiths, J. B., Newell, D. G. Cell & Tissue Culture: Laboratory Procedures 1993, John Wiley & Sons. Each of these references is hereby incorporated in its entirety. There are further methods in the art for the preparation and maintenance of cell cultures under animal derived component-free and protein-free conditions (including methods concerning CHO cells) such as those seen in International Patent Application No. WO97/05240, No. WO 96/26266, and No. WO 00/11102, U.S. Pat. Nos. 6,100,061, 6,475,725, and 8,084,252. Each of the preceding documents is hereby incorporated by reference in its entirety. In one embodiment of the present invention, animal-derived component (ADC)-free medium can be used. Conventional synthetic minimal media may contain inorganic salts, amino acids, vitamins, a carbohydrate source, and water. In a specific embodiment of the present invention, the medium that may be used is CD-CHO (GIBCO, Invitrogen Corp.; an animal origin-free medium that is chemically defined and contains no proteins, hydrolysates, or components of unknown origin). Additionally, the medium may have additional components including glutamine and/or methotrexate or other factors which may aid in growth or adherence. In a specific embodiment, the additional component may be GLUTAMAX-1 or L-glutamine added at between about 2 mM and about 8 mM, e.g. at about 2 mM, about 3 mM, about 4 mM, about 5 mM, about 6 mM, about 7 mM, or about 8 mM.

ii. Host Cells and Expression Vectors

In certain embodiments, the cells employed in the cell banking process of the invention are host cells harboring an expression construction for expression of a therapeutically relevant protein or other polypeptide of interest. Any cell that can be used to express a polypeptide of interest (e.g. a binding polypeptide) can be used according to the methods described herein. The cells may optionally contain naturally occurring or recombinant nucleic acid sequences, e.g. an expression vector that contains a polypeptide of interest. The expression vector may optionally contain appropriate transcriptional and translational controls and may be constructed using recombinant DNA technology known in the art. Expression vectors may be transferred to any host cell by techniques known in the art, and the transformed cells may then be cultured according to the method of the present invention to create a high-density cell bank. Furthermore, the high-density cell bank may then be thawed and cultured according to techniques known in the art in order to produce the encoded protein of interest and, where desired, this protein may be subsequently purified.

In certain embodiments, a variety of host expression systems can be used to produce therapeutically relevant proteins. Furthermore, the host expression system may be a mammalian cell system (e.g., CHO, CHO-DBX11, CHO-DG44, CHO-S, CHO-K1, Vero, BHK, HeLa, COS, MDCK, HEK-293, NIH-3T3, W138, BT483, Hs578T, HTB2, BT20, T47D, NSO, CRL7030, HsS78Bst cells, PER.C6, SP2/0-Ag14, and hybridoma cells) harboring recombinant expression constructs containing promoters derived from the genome of mammalian cells. Viral-based expression systems can also be utilized in concert with mammalian cells (see, e.g., Logan et al, 1984, Proc. Natl. Acad. Sci. USA 8:355-359, hereby incorporated by reference in its entirety). The efficiency of expression can be enhanced by the inclusion of elements including (but not limited to) appropriate transcription enhancer elements and transcription terminators (see, e.g., Bittner et al., 1987, Methods in Enzymol. 153:516-544, hereby incorporated by reference in its entirety).

In other embodiments, a host cell strain can be chosen that modulates the expression of the inserted sequences or that modifies and processes the gene product in the specific fashion desired. Different host cells have characteristic and specific mechanisms for the post-translational processing and modification of proteins and gene products. Appropriate cell lines or host systems can be chosen to ensure the correct modification and processing of the polypeptide (e.g., a binding polypeptide) expressed. Such cells include, for example, established mammalian cell lines and animal cells, as well as insect cell lines, fungal cells, and yeast cells.

iii. Bioreactors

Any bioreactor suitable for culturing cells under perfusion culture conditions may be employed in the methods of the invention. The bioreactor may be inoculated using an aliquot of cells at an appropriate seed density (such as a vial of cells or cells from a starter culture, e.g. a shake flask or a shake flask seed train that have been cultured to that density). The appropriate seed density for a culture depends on several factors including the type of cells used and the bioreactor being inoculated. The appropriate seed density can be determined using methods available in the art.

In certain embodiments, the bioreactor may be of a disposable nature, for example the bioreactor can be a flexible bag or a plastic flask that is connected to the cell retention device by means of flexible tubing. It may have a volume of about 1 L, 2 L, 5 L, 10 L, about 20 L, 50 L, 75 L, 85 L, 100 L, 150 L or about 400 L. In a specific embodiment of the invention, the bioreactor is a 10 L flexible bag that has been customized with two dip tubes i.e. tubes that are used to remove medium or product. Exemplary disposable bioreactors are WAVE® cellbag bioreactors (GE Healthcare, Pittsburgh, Pa.) such as the 20 L WAVE® bioreactor. These are the perfusion bioreactor systems described in, among other documents: Singh, 1999, Disposable bioreactor for cell culture using wave-induced agitation, *Cytotechnology*, p.149-158, hereby incorporated by reference in its entirety.

The working volume of the reactor is the volume occupied by culture. The working volume can be, for example, 10%, 20%, 30%, 40%, 50%, 60%, 70% or more of the culture, but preferably not more than 75%.

Alternatively, the bioreactor may be of a non-disposable nature. For example, the bioreactor can be made of stainless steel or glass. Alternative bioreactors suitable for use in the present invention include, but are not limited to: shake flasks, stirred tank vessels, airlift vessels, and disposable bags that can be mixed by rocking, shaking, or stirring.

In an embodiment, the bioreactor may be coupled to a cell retention system, including, but not limited to, built-in filters, spin basket TFF systems, and ATF systems.

II. Non-centrifugal Concentration

Perfusion culture depends on the ability to remove nutrient-depleted and waste product-containing media from the culture while minimizing damage to the cells. Initial methods of cell retention, in which the depleted medium is separated from cultured cells, frequently damaged the cells through inherent problems such as the creation of shear forces. This eventually results in the clogging of filters and the failure of the perfusion devices, many of which were internal to the culture system. Accordingly, in one aspect, the current disclosure provides a method that makes use of a "cell retention system" that allows for media exchange and is then used to further concentrate the cell culture for cryobanking.

In one embodiment, the type of cell retention system used is a "built in" type filter, wherein the filter is disposed in the chamber of the bioreactor and is free to move within the chamber. The filter may be coupled to one of the tubes leading out of the chamber, thereby allowing filtered medium to be drawn from the culture. One example of a "built in" type filter may be found in U.S. Pat. No. 6,544,788, which is hereby incorporated by reference in its entirety.

In another embodiment, the cell retention system used is a tangential flow filtration system (TFF). In a TFF system, culture medium is circulated from a culture vessel through a filtration module, and then back to the culture vessel by means of a pump attached to the tubing between the filtration module and the culture vessel, producing a tangential flow across the filter module. A second pump is positioned on the filtrate side of the filter module and is used to control the rate at which filtrate is removed. The use of hollow-fiber membrane filters is preferred in this system as they are easier to sterilize and allow for the maintenance of a uniform flow across the filter module. However, when hollow fiber filters are employed in this system, they are prone to clogging as the mono-directional flow leads to the aggregation of particulate matter at the lumen inlet.

In a specific embodiment, the type of cell retention system used is an alternating tangential flow (ATF) system. In the ATF type of cell retention system, a filtering compartment is connected to a storage vessel at one end and a diaphragm pump at the other. The pump first moves medium from the vessel through the filter element to the pump and then reverses to send the medium from the pump through the filter and back to the vessel, creating a bi-directional or alternating flow. This is referred to as alternating tangential flow (ATF) as there is alternating tangential flow at the filter module, i.e. there is one flow in the same direction to the membrane surfaces of the filter module (tangential to that surface), and that there is another flow that is substantially perpendicular to those surfaces. This type of filtration has been extant in the literature since 2000 and results in rapid, low shear, uniform flow. ATF filtration can be obtained by methods known in the art, such as are described in U.S. Pat. No. 6,544,424, which is hereby incorporated by reference in its entirety. Furthermore, alternating tangential flow systems are available commercially from manufacturers such as Refine Technology and include various models such as the ATF2, ATF4, ATF6, ATF8, and ATF10 systems.

In another specific embodiment of the invention, the filter is a tubular membrane filter, and furthermore may be a hollow fiber filter.

As indicated above, the methods of the invention allow for non-centrifugal concentration of cells at high densities. In a particular embodiment of the invention, the culture is grown to a density of at least $1\times10^7$ cells/mL, e.g. to about $1\times10^7$ cells/ml, about $2\times10^7$ cells/ml, about $3\times10^7$ cells/ml, about $4\times10^7$ cells/ml, about $5\times10^7$ cells/ml, about $6\times10^7$ cells/ml, about $7\times10^7$ cells/ml, or about $8\times10^7$ cells/ml, and following that period of growth there is a further concentrating step that is performed using non-centrifugal methods. This concentrating step may concentrate the culture to a density of at least $5\times10^7$ cells/mL, e.g. about $5\times10^7$ cells/mL, $6\times10^7$ cells/mL, $7\times10^7$ cells/mL, $8\times10^7$ cells/mL, $9\times10^7$ cells/mL, $10\times10^7$ cells/mL, $11\times10^7$ cells/mL, $12\times10^7$ cells/ml, $13\times10^7$ cells/mL, $14\times10^7$ cells/mL, $15\times10^7$ cells/mL, $16\times10^7$ cells/mL, or $17\times10^7$ cells/mL. The non-centrifugal method used to further concentrate the culture may make use of any cell retention system known in the art (e.g. a "built in" type filter, a TFF system, or an ATF system including those described above).

III. Cryopreservation and Cell Banking

Cryopreservation refers to a process by which cells, tissues, or any other substances susceptible to damage caused by time or by enzymatic or chemical activity are preserved by cooling and storing them to sub-zero temperatures. The importance of cryopreservation of important cell lines cannot be underestimated, as (among other important advantages) this allows the maintenance of these lines without maintaining them in constant culture, decreases the risk of contamination, and reduces the risk of genetic drift.

When using cryopreservation methods, it is vital to reach and stay at these low temperatures without causing additional damage through the formation of ice during the freezing process. Methods in the art traditionally use substances that decrease freezing damage to cells called cryoprotectants. Cryoprotectants may be added to the medium of cell cultures prior to the freezing process. In a specific embodiment, the cryoprotectant used may be one or more of: glycerol or dimethyl sulphoxide (DMSO). Additionally, the cryoprotectant may be added with or without hydroxyethyl starch (HES). In a further specific embodiment, DMSO may be added at a concentration of at least 5%, e.g. it may be added at about 5%, about 6%, about 7%, about 8%, about 9%, about 10%, about 11%, about 12%, about 13%, about 14%, about 15%, about 16%, about 17%, at about 18%, about 19%, or at about 20%.

The culture with added cryoprotectant may then be dispensed into containers appropriate for storage under cryopreservation conditions. In one embodiment, this container may be a vial made of a material which may include (but is not limited to) polymers such as polytetrafluoroethylene, polystyrene, polyethylene, or polypropylene. In a specific embodiment, the vial may have an additional surface treatment in order to improve cryopreservation conditions (e.g. hydrophilic coatings which reduce adsorption and denaturation). In exemplary embodiments, the vial may have a volume of more than about 0.1 mL, e.g. the vial may have a volume of about 0.1 mL, about 0.5 mL, about 0.75 mL, about 1 mL, about 2 mL, about 2.5 mL, about 5mL, about 10 mL, about 15 mL, about 20 mL, about 25 mL, or about 50 mL. In another embodiment, the container may also be a cryobag. The cryobag may be constructed of any appropriate material including, but not limited to, polymers such as polytetrafluoroethylene, polystyrene, polyethylene, polypropylene, Fluorinated Ethylene Propylene (FEP) and ethylene vinyl acetate (EVA). Exemplary disposable bioreactors include but are not limited to: KryoSure® Cryopreservation bags, PermaLife™ Bags (OriGen Biomedical), CryoStore freezing bags, Freeze-Pak™ Bio-containers.

These containers are then frozen using techniques and devices well known in the art before being stored at low temperatures, typically between about −130° C. and about −195° C. In one embodiment the freezing technique used may be control-rate and slow freezing (also called slow programmable freezing, or SPF).The collection of cells obtained by the process is a cell bank.

In an embodiment, the cell bank may be, but is not limited to, a high density cell bank, a master cell bank, or a mini bank.

IV. Determination of Cell Viability

As indicated above, the methods of the invention allow for cell banking at high densities while retaining excellent cell viability for later use. As used herein, the term "cell viability" can be defined as the number or percentage of healthy cells in a given sample. The viability of cells may be determined using any method available in the art at any point in the high density cell banking process described. Commonly used methods for the determination of cell viability are largely based on the principle that live cells possess intact cell membranes that exclude certain dyes, such as trypan blue (a diazo dye), Eosin, or propidium, whereas dead cells do not.

In one embodiment, trypan blue can be used to stain a quantity of cells and thereby indicate the presence of cells with intact membranes (not colored) and the presence of cells with disrupted membranes (blue). These cells may then be counted to determine the numbers of both live and dead cells in the culture, and presented as a percentage to indicate the relative health of the culture.

In a specific embodiment the cell viability may be determined using a culture that has been concentrated, but has not yet been frozen (i.e. a pre-freezing culture). In a specific embodiment the cell viability may be determined using a culture that has been concentrated, frozen, and then thawed (i.e. a post-thaw culture).

In a specific embodiment, the cell viability may be more than about 60%, e.g. about 60%, 65%, 70%, 75%, 80%, 85%, 90%, or 95%. In certain embodiments, the post-thaw viability of the cells is more than about 80%, e.g., more than 85%, 90%, or 95% including up to100%.

Apoptosis is programmed cell death and is an active regulatory pathway of cell growth and proliferation. Cells respond to specific induction signals resulting in characteristic physiological changes. Among these is the externalization of phosphatidylserine (PS) to the cell outer surface during the early apoptotic pathway. The Guava Nexin® Assay utilizes Annexin V-PE (a calcium-dependent phospholipid binding protein with high affinity for PS) to detect PS on the external membrane of apoptotic cells. The cell impermeant dye, 7-AAD, is also used as an indicator of cell membrane structural integrity. 7-AAD is excluded from live, healthy cells as well as early apoptotic cells. Three populations of cells can be distinguished in this assay:
1) Non-apoptotic cells (or healthy cells):
2) Annexin V(−) and 7-AAD(−).
3) Early apoptotic cells: Annexin V(+) and 7-AAD(−)
4) Late stage apoptotic and dead cells: Annexin V(+) and 7-AAD(+)

Figure 4:
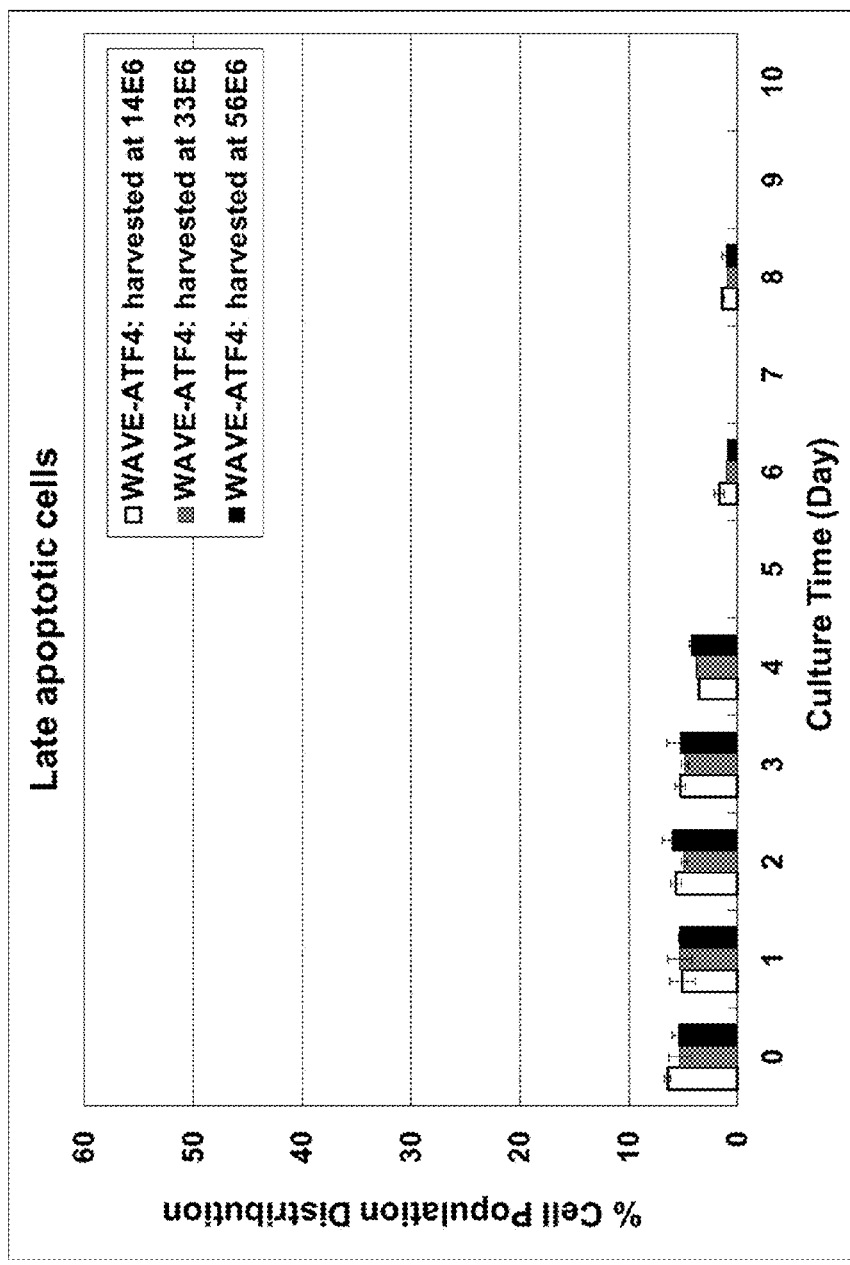
FIG. 4: is a graphic of the post banking performance (late apoptosis) of mini-banks made using cultures harvested at multiple time points during growth.
Figure 7:
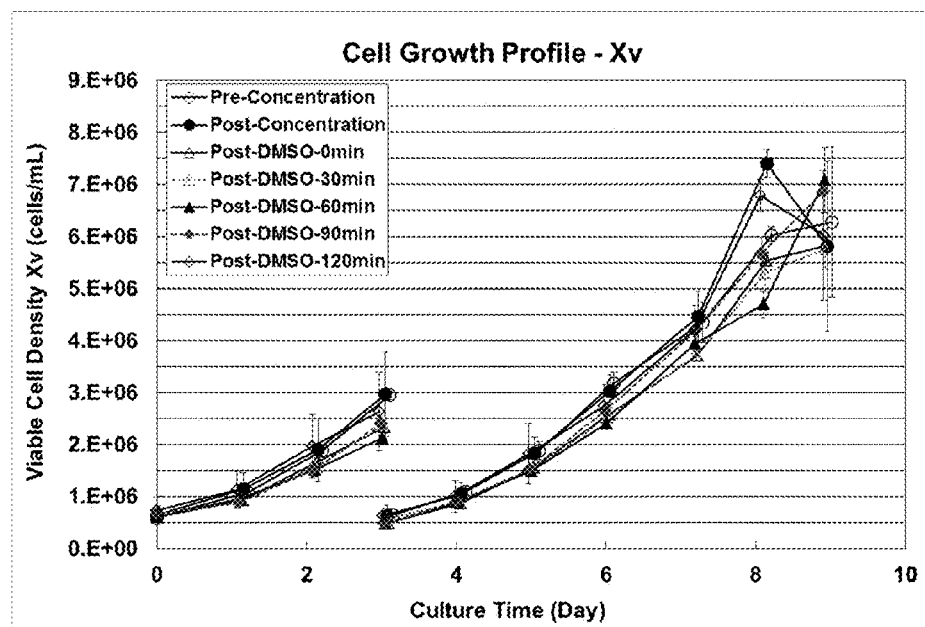
FIG. 7A-B: is a chart of the viable cell density (A) and late apoptosis (B) of cells at different stages: pre-concentration, post concentration, and after 0 to 120 min of exposure to DMSO.
Figure 7:
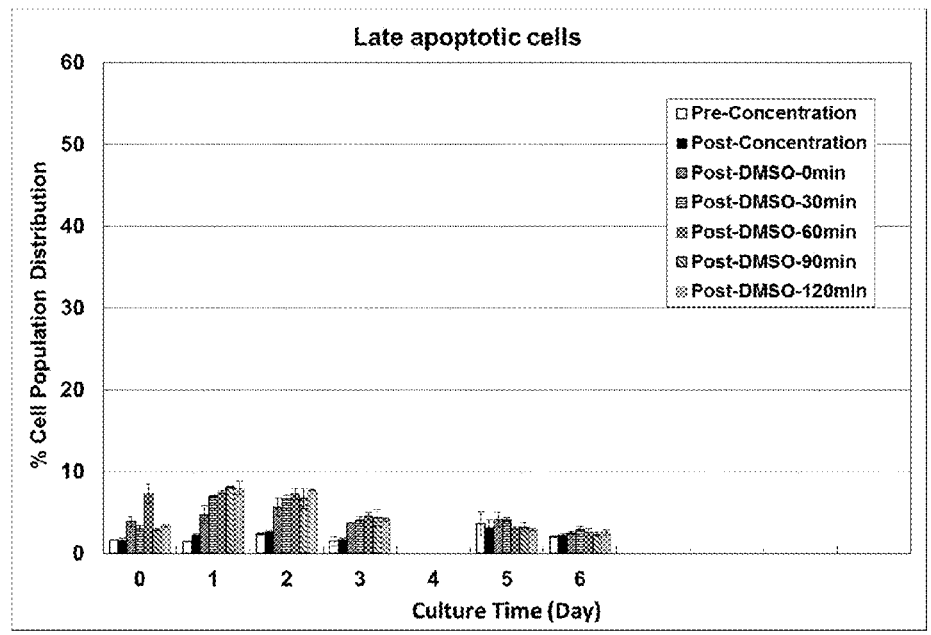

The amount of late apoptotic cells is another measure of the health of post thaw cultures and can be monitored as shown in FIGS. 4 and 7B. In a specific embodiment, the post thaw late apoptotic cells should be less than 30% of the viable cell population. In a another embodiment, the post thaw late apoptotic cells should be less than 20% of the viable cell population. In a another embodiment, the post thaw late apoptotic cells should be less than 10% of the viable cell population.

V. Therapeutically Relevant Proteins

Cells derived from the high-density cell cryobanking method of the invention can be employed in a later production phase for the manufacture of a protein. For example, the cells propagated in the bioreactor and frozen in high-density bank aliquots according to the methods of the present invention may be used for the production of biological substances including therapeutically relevant proteins. These biological substances may include, but are not limited to: viruses (see e.g. WO200138362), binding polypeptides such as antibodies, e.g. monoclonal antibodies, and fragments thereof, e.g. fab fragments; Fc fusion proteins, anticoagulants, blood factors, bone morphogenetic proteins, engineered protein scaffolds, enzymes, growth factors, hormones, interferons, interleukins, and thrombolytics. These biological substances can be harvested using any method available in the art. In one embodiment, the invention provides a method of producing a biological substance, the method comprising: culturing cells capable of expressing a biological substance under conditions suitable for the production of a biological substance, wherein the cells were obtained from a high-density frozen cell bank produced using perfusion culture and non-centrifugal concentration methods. The biological substance may be (but is not limited to) a protein (e.g. any therapeutically relevant protein).

EXAMPLES

The present invention is further illustrated by the following examples which should not be construed as further limiting. The contents of the figures and all references, patents, and published patent applications cited throughout this application are expressly incorporated herein by reference in its entirety.

Example 1

Design and Implementation of a High-density Cell Banking Protocol

This high-density cell cryobanking protocol begins with a 2 mL master cell bank vial of cells (working volume 1.5 mL) at an approximate density of 2.0-2.4×10^7 viable cells/mL (normal cell cryopreservation condition). The cells are then grown in perfusion culture and concentrated via alternating tangential flow. Following the addition of DMSO to the concentrated cell culture, this high density cell culture is dispensed into approximately 200 separate 5 mL vials (approximately 4.5 mL working volume) for storage as a high density cell bank (approximately 10×10^7 cells/mL).

Example 2

Determination of Optimal Cell Retention Methods for the Support of Fast Cell Growth and Concentration Speed In order to determine the optimal cell retention method for use in the creation of a high density cell culture banking system (FIG. 1), the built-in floating filter in the standard GE perfusion bioreactor, TFF (tangential flow filtration), ATF2, and ATF4 were evaluated for their ability to support increased cell growth and viable cell density under defined parameters (Table 1).

TABLE 1

Experimental parameters used for comparison of cell retention methods

| Parameter | Detailed Description |
| --- | --- |
| Cell line | rCHO cell line 1 |
| Seed train medium | CD CHO with glutamine and methotrexate |
| Bioreactor medium | CD CHO with glutamine |
| Bioreactors | Standard GE10-L Cellbag perfusion bioreactor; custom 10-L Cellbag perfusion bioreactor with two dip tubes |
| Bioreactor working volume | 5 L |
| Cell retention methods | built-in floating filter (0.2 pm) in the standard GE perfusion bioreactor, TFF (0.2 μm), TFF (0.65 μm), ATF2 (0.2 μm), ATF4 (0.2 μm) |
| Bioreactor inoculum | shake flask seed train |
| Bioreactor seed density | ~5 × 10^5/mL |
| Cell specific perfusion rate | ≥0.2 nL/cell-day |
| pH | 7.0 ± 0.1 |
| DO | ≥40% |

Figure 2:
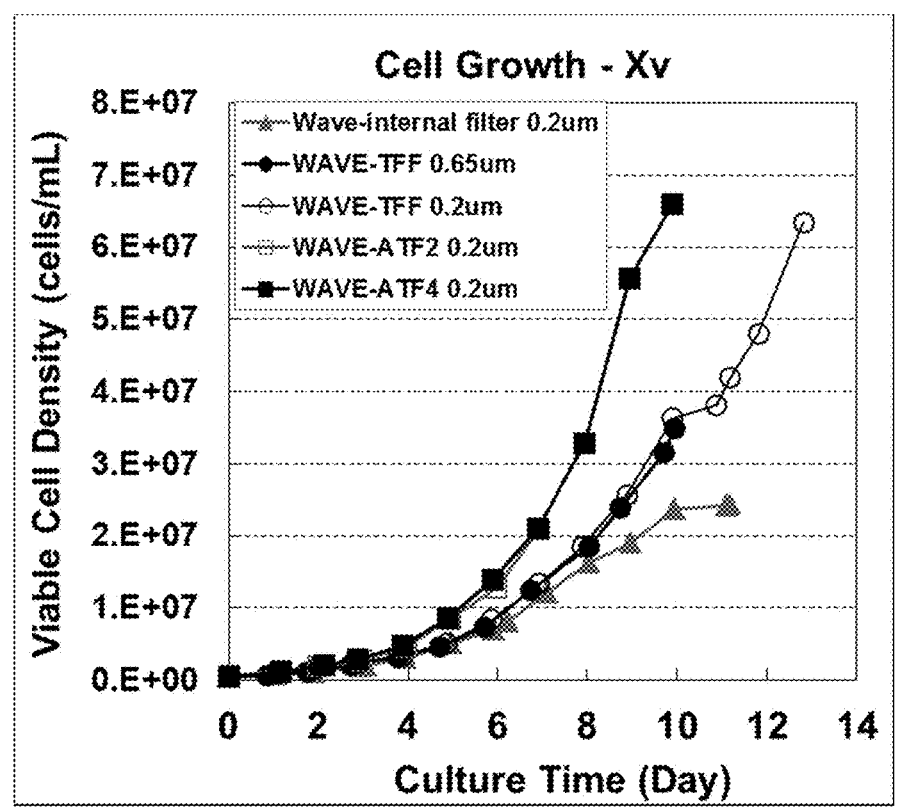
FIG. 2: is a chart depicting cell growth profiles of WAVE® perfusion cultures using different cell retention methods.
Figure 11:
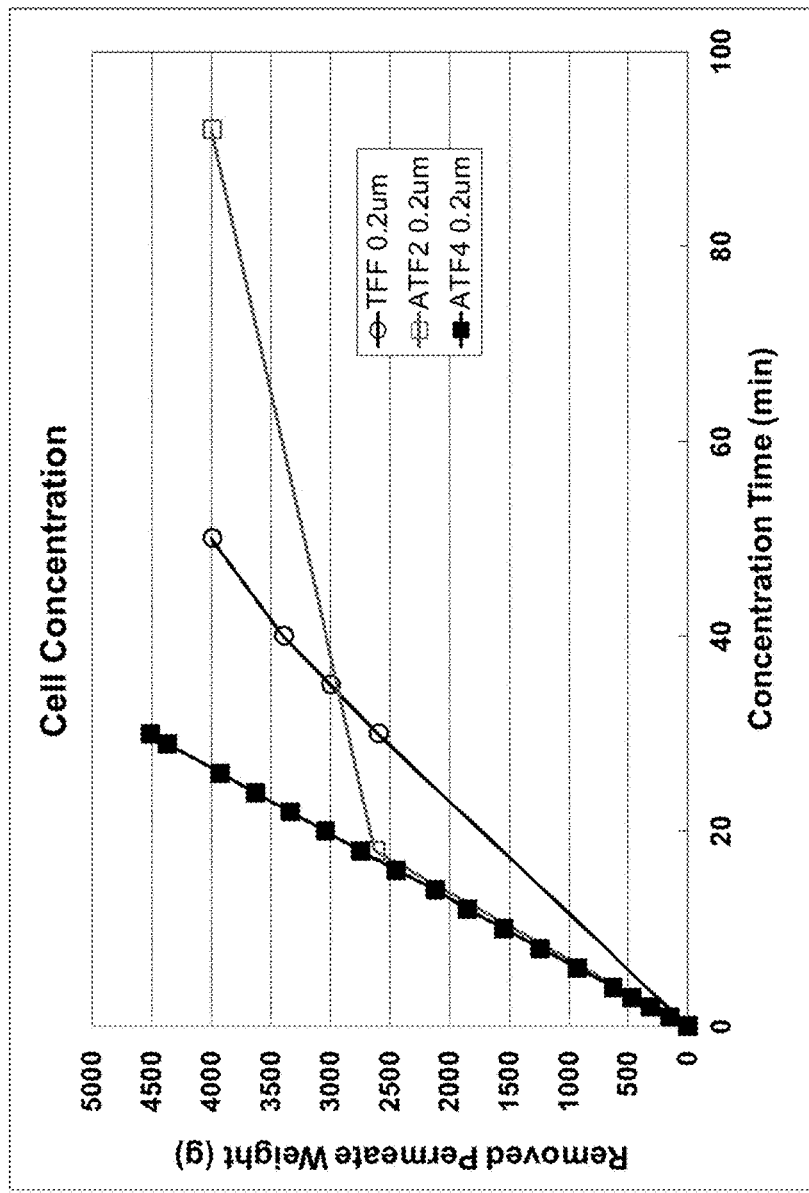
FIG. 11: is a chart indicating the concentration of cultures over time using different cell retention systems.

The ATF4 alternating tangential flow system supported the faster cell growth achieved using these parameters along with a rapid (30 min) final 4-fold culture concentration without filter fouling. Other methods under examination resulted in lower concentrations of viable cells per mL, demonstrated a lower concentration efficiency, and/or resulted in fouling during culturing and/or concentration. These results can be seen in FIG. 2, FIG. 11, and Table 2.

TABLE 2

Results from comparison of different cell retention methods

| Retention Method | Max Xv (viable cells/mL) | DT (Hours) | Concentration Speed | Operational Comments |
| --- | --- | --- | --- | --- |
| ATF4; 0.2 μm | 6.6 × 10^7 | 32 | 30 mins; 4X | Partially disposable, easy operation |

TABLE 2-continued

Results from comparison of different cell retention methods

| Retention Method | Max Xv (viable cells/mL) | DT (Hours) | Concentration Speed | Operational Comments |
|---|---|---|---|---|
| Built-in filter 0.2 μm | $2.4 \times 10^7$ | 36 | 20 mins; 2X | Filter clogged during concentration |
| TFF 0.2 μm | $6.3 \times 10^7$ | 37 | 50 mins; 3X | Cartridge clogged during culturing, total two cartridges used |
| TFF 0.65 μm | $3.5 \times 10^7$ | 34 | N/A | Cartridge clogged during culturing |
| ATF2 0.2 μm | $2.1 \times 10^7$ | 34 | 90 mins; 5X | Partially disposable |

Example 3

Determination of Optimal Time to Harvest Cultured Cells for Concentration and High-density Banking To determine the optimal cell harvesting timing for subsequent final concentration and high-density cell cryobanking, cultures of rCHO cell line 1 were grown in a custom 10-L WAVE® (GE Healthcare Life Sciences) cellbag bioreactor under perfusion culture conditions that used an alternating tangential flow system. Cells at different cell densities ($14 \times 10^6$, $33 \times 10^6$, $56 \times 10^6$/mL) were collected at multiple time points during the perfusion culture to make mini banks (FIG. 1).

These banks were evaluated by comparing the post-thaw quality of the cells in terms of growth rate, viability, and cell death (apoptosis). The parameters under which these cells were grown during the initial culture and in post-banking evaluation are shown in Table 3.

TABLE 3

Experimental parameters used for determination of the timing for optimal cell harvest

| Parameter | Detailed Description |
|---|---|
| Cell line | rCHO cell line 1 |
| Seed train medium | CD CHO with glutamine and methotrexate |
| Bioreactor medium | CD CHO with glutamine |
| Bioreactors | custom 10-L Cellbag perfusion bioreactor with two dip tubes |
| Bioreactor working volume | 5 L |
| Cell retention methods | ATF4 (0.2 μm) |
| Bioreactor inoculum | shake flask seed train |
| Bioreactor seed density | $\sim 5 \times 10^5$/mL |
| Cell specific perfusion rate | $\geq 0.2$ nL/cell-day |
| pH | $7.0 \pm 0.1$ |
| DO | $\geq 40\%$ |
| Post banking evaluation | Shake flask seed train for three passages; viable cell density (Xv), viability, and apoptosis were evaluated |
| Post banking evaluation seed train medium | CD CHO with glutamine |

Figure 3:
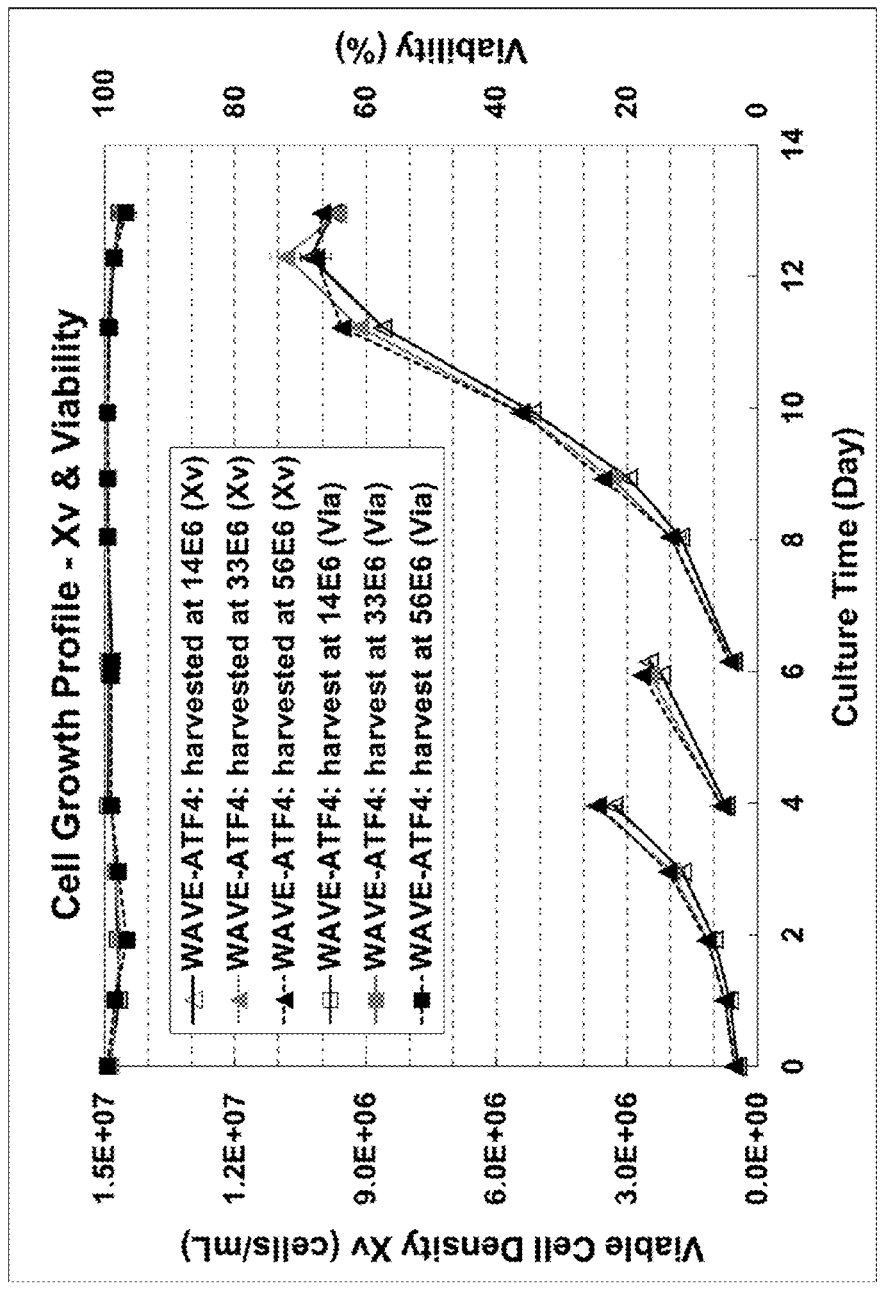
FIG. 3: is a graphic of the post banking performance (viable cell density (Xv), viability) of mini-banks made using cultures harvested at multiple time points during growth.

The post-thaw cell performance of the mini banks made at different cell densities from these cultures were comparable in terms of their cell growth rate, viability (FIG. 3), and apoptosis rate (FIG. 4). These data indicate that the cells are healthy and ready for harvest up to approximately $60 \times 10^6$ cells/mL.

Harvest densities of approximately $(30-40) \times 10^6$ cells/mL were selected in order to shorten the culture period and to make the process more practicable. These cultures are then further concentrated to $>11 \times 10^7$ cells/mL in 30 minutes using an alternating tangential flow system.

Example 4

Determination of Optimal WAVE® Parameters During High-density Cell Culture

To make this high density cell culturing and banking process more robust and GMP implementable, WAVE® operation parameters were studied and defined in order to establish a system in which this culture could be maintained in the absence of automatic pH and DO controls.

These WAVE® operation parameters were tested in a perfusion culture system combined with an alternating tangential flow system defined using the parameters seen in Table 4.

TABLE 4

Experimental parameters used for determination of WAVE® operation parameters.

| Parameter | Detailed Description |
|---|---|
| Cell line | rCHO cell line 1 |
| Seed train medium | CD CHO with glutamine and methotrexate |
| Bioreactor medium | CD CHO with glutamine |
| Bioreactors | custom 10-L Cellbag perfusion bioreactor with two dip tubes |
| Bioreactor working volume | 5 L |
| Cell retention methods | ATF4 (0.2 μm) |
| Bioreactor inoculum | shake flask seed train |
| Bioreactor seed density | $\sim 5 \times 10^5$/mL |
| Cell specific perfusion rate | $\geq 0.2$ nL/cell-day |
| pH | $7.0 \pm 0.1$ (with and without pH feedback control) |
| DO | $\geq 40\%$ (with and without DO feedback control) |

An oxygen mass transfer ($k_L a$) study shows that WAVE® rock rate and angle are key parameters that affect oxygen transfer. Furthermore, the headspace concentration of both oxygen and carbon dioxide can significantly affect DO and pH.

Simplified bioreactor operation condition including WAVE® rocking and gassing adjustment (Table 5) combined with a high perfusion rate were applied to achieve target DO and pH levels without automatic control.

TABLE 5

WAVE® Operation Parameters during Growth without pH and DO Control

| Parameter | Initial Set points |
|---|---|
| Rock speed (rpm) | 22 |
| Rock angle (°) | 10 |
| Temperature (° C.) | 37 |
| Air flow rate (lpm) | 0.2 |
| $CO_2^1$ | 10 |
| $O_2^2$ | 20 |

When the offline pH as measured by Blood Gas Analyzer (BGA) was $\leq 6.9$, the CO2 set point was reduced from 10% to 5%. If the offline pH measured $\leq 6.9$ again, the CO2 set point was reduced from 5% to 0%. If offline pH was still $\leq 6.9$, the perfusion rate was increased. When the DO was measured at $\leq 45\%$, the O2 set point was raised from 20% to 30%. If the DO measured $\leq 45\%$ again, the rock speed was increased to 25 rpm and the rock angle was changed to 12°. Additionally, the O2 level was raised from 30% to 40%.

This method was further refined by adjusting the rock rate (Table 6) during the final concentration step to avoid the inclusion of air into the ATF4 system.

TABLE 6

WAVE ® Operation Parameters during Concentration

| Bioreactor volume | WAVE ® stop angle (°) | Rock speed (rpm) | Rock angle (°) |
| --- | --- | --- | --- |
| 3.5 L–~5 L | N/A | 15 | 8 |
| 2.5 L-3.5 L | N/A | 5 | 5 |
| ~1.5 L-2.5 L | 10 | 0 | 0 |

Figure 5:
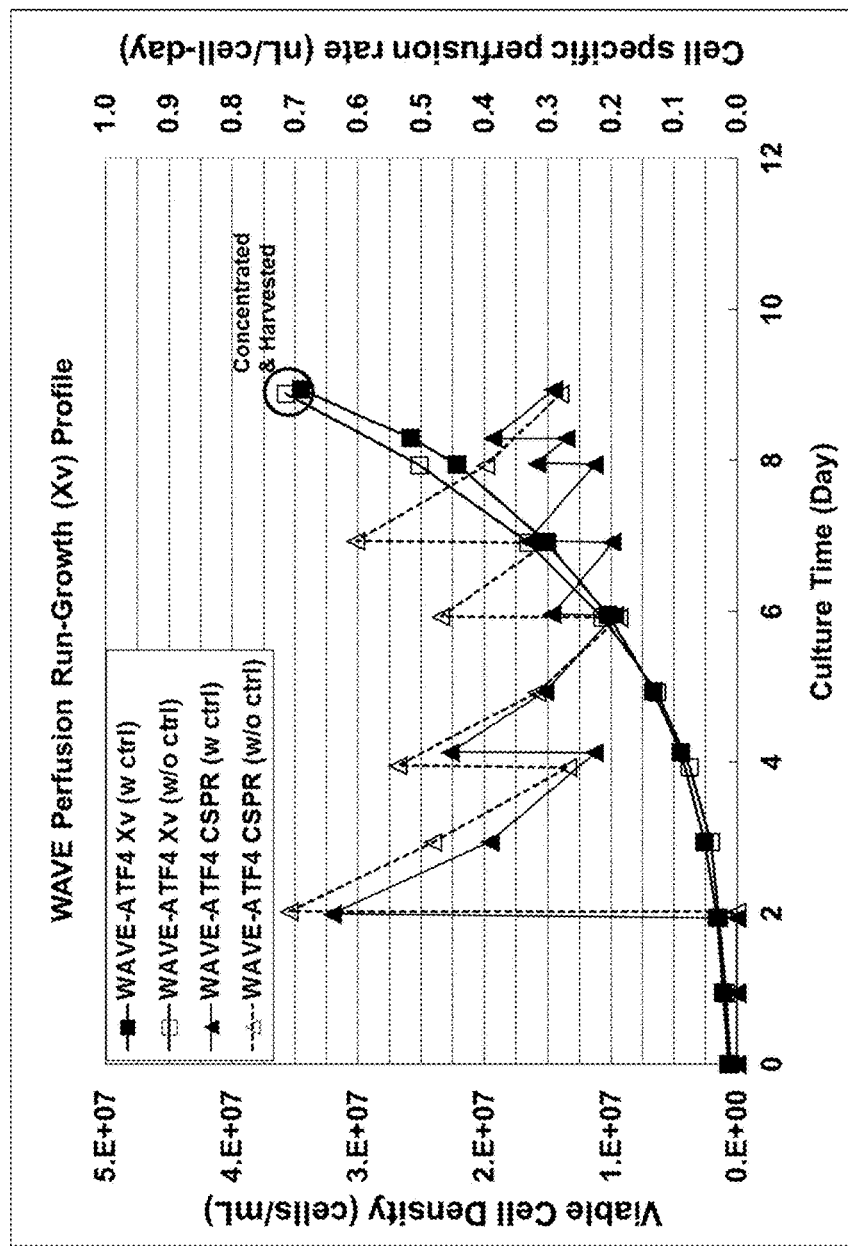
FIG. 5: is a chart showing cell growth with and without automated pH and DO feedback controls.
Figure 6:
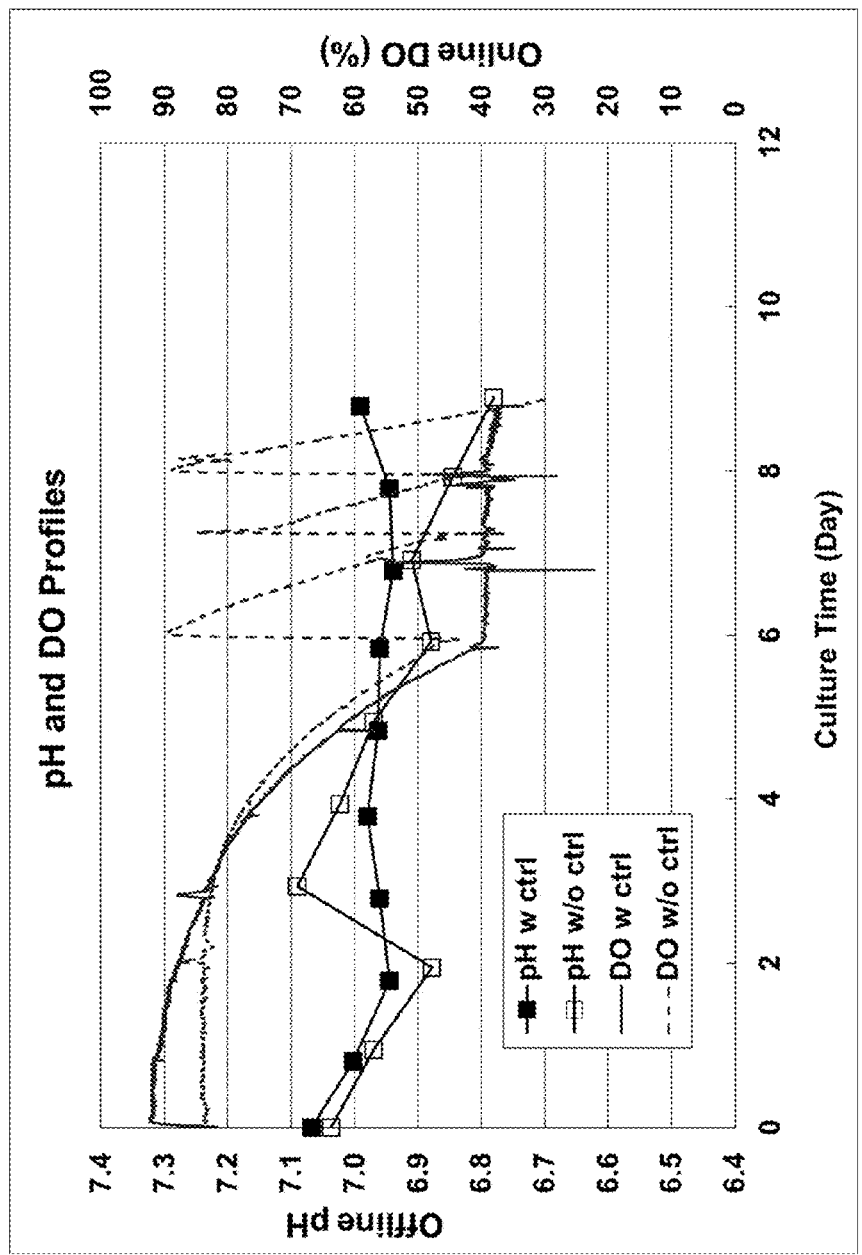
FIG. 6: is a chart showing pH and DO profiles with and without automated pH and DO feedback controls.

A simplified set of bioreactor operating conditions including WAVE® rocking and gassing adjustment resulted in comparable cell growth performance without relying on automated pH and DO feedback controls, FIGS. 5 and 6. The rocking adjustment also resulted in minimal air inclusion during the ATF4 concentration step.

Example 5

Determination of the Effect of the ATF Concentration Step and DMSO Exposure on Cell Health In order to determine the effect of the ATF4 concentration step and the pre-freezing DMSO exposure on cell quality, shake flasks were inoculated with live cells collected at different stages in the high-density cell banking procedure for growth evaluation. The samples collected and examined under the conditions shown in Table 7 were: pre-concentration, post concentration, and with a DMSO exposure length of 0 to 120 min.

TABLE 7

Experimental parameters used for determination of WAVE ® operation parameters.

| Parameter | Detailed Description |
| --- | --- |
| Cell line | rCHO cell line 1 |
| Seed train medium | CD CHO with glutamine and methotrexate |
| Bioreactor medium | CD CHO with glutamine |
| Bioreactors | custom 10-L Cellbag perfusion bioreactor with two dip tubes |
| Bioreactor working volume | 5 L |
| Cell retention methods | ATF4 (0.2 μm) |
| Bioreactor inoculum | shake flask seed train |
| Bioreactor seed density | ~5 × 10$^5$/mL |
| Cell specific perfusion rate | ≥0.2 nL/cell-day |
| pH | 7.0 ± 0.1 (with and without pH feedback control) |
| DO | ≥40% (with and without DO feedback control) |
| Cell quality evaluation | Viable cell density (Xv), viability, apoptosis |
| Cell quality evaluation seed train medium | CD CHO with glutamine |

The cell growth (FIG. 7A) and apoptosis rate (FIG. 7B) of pre-concentration cells and post concentration cells were comparable as were the cell growth and apoptosis rates of cells with different lengths of exposure to DMSO. This suggests that in-vessel 30-min ATF4 concentration and full scale dispensing of over 200 vials in 90 min while maintaining the pre-freezing cell quality is feasible.

Example 6

Determination of Post-banking Cell Quality and the Applicability of the Platform to Multiple Cell Lines To determine the post-banking cell quality of the high-density cell banks, post-thaw cells were cultured and examined to determine their relative cell growth rates, viability, and levels of apoptosis. Furthermore, three different cell lines (rCHO cell lines 1, 2, and 3) were employed in order to ensure that this platform could be readily applied to other cell lines. The experimental conditions under which these cells were grown pre- and post-banking are detailed in Table 8.

TABLE 8

Experimental parameters used for the post-banking cell quality of the HD banks for multiple cell lines.

| Parameter | Detailed Description |
| --- | --- |
| Cell line | rCHO cell lines 1, 2, and 3 |
| Seed train medium | CD CHO with glutamine and methotrexate for rCHO cell line 1, CD CHO with glutamine for rCHO cell lines 2 and 3 |
| Bioreactor medium | CD CHO with glutamine |
| Bioreactors | custom 10-L Cellbag perfusion bioreactor with two dip tubes |
| Bioreactor working volume | 5 L |
| Cell retention methods | ATF4 (0.2 μm) |
| Bioreactor inoculum | shake flask seed train |
| Bioreactor seed density | ~5 × 10$^5$/mL |
| Cell specific perfusion rate | ≥0.2 nL/cell-day |
| pH | 7.0 ± 0.1 (without pH feedback control) |
| DO | ≥40% (without DO feedback control) |
| Post banking evaluation | shake flask seed train for up to three passages; viable cell density (Xv), viability, and apoptosis were evaluated |
| Post banking evaluation seed train medium | CD CHO with glutamine |

Figure 8:
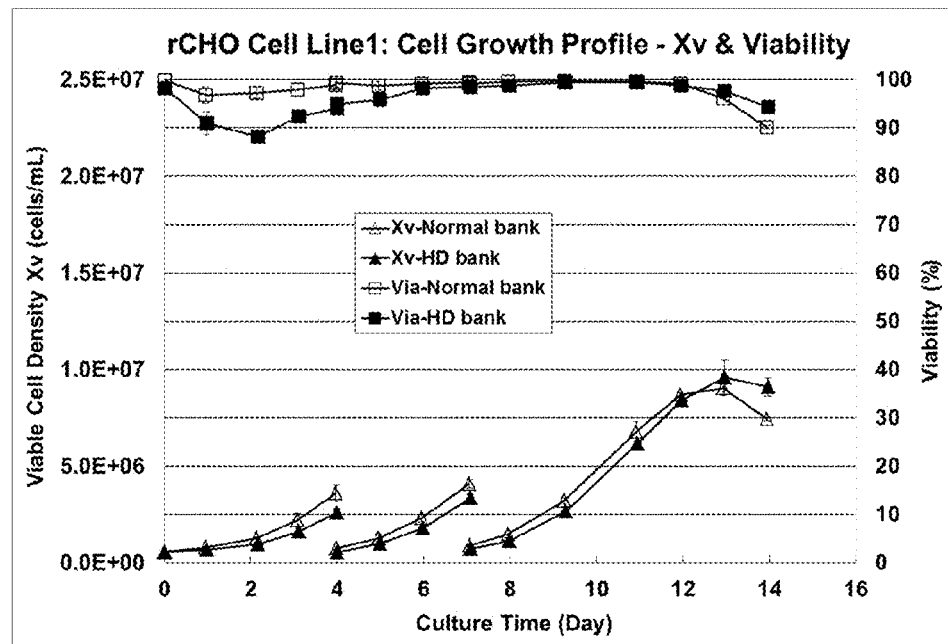
FIG. 8A-B: is a chart of the post-banking performance (A) and late apoptosis (B) of the rCHO cell line 1 high density bank as compared to a normal density bank.
Figure 8:
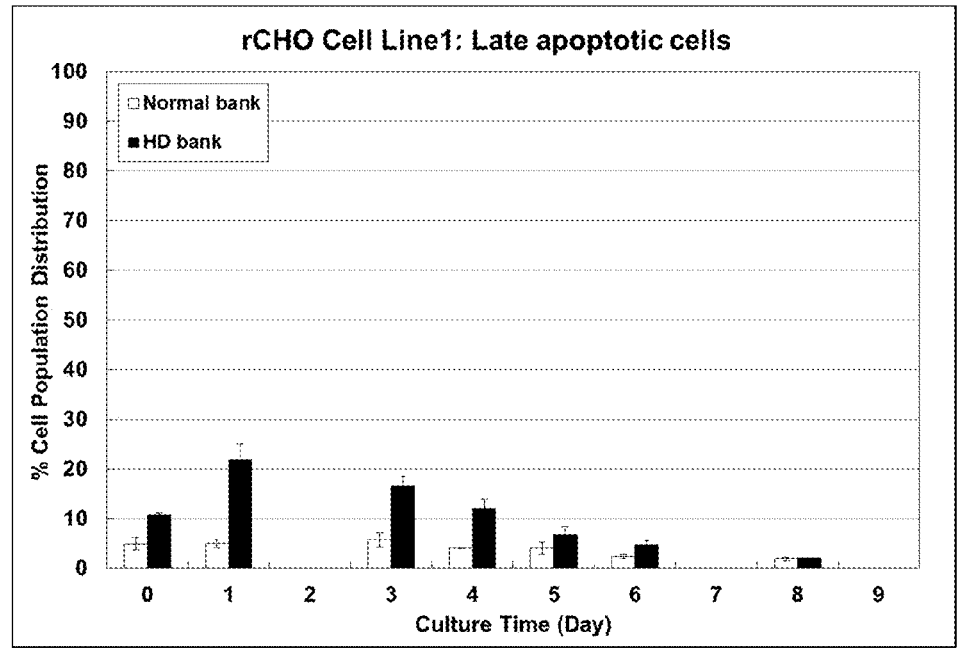
Figure 9:
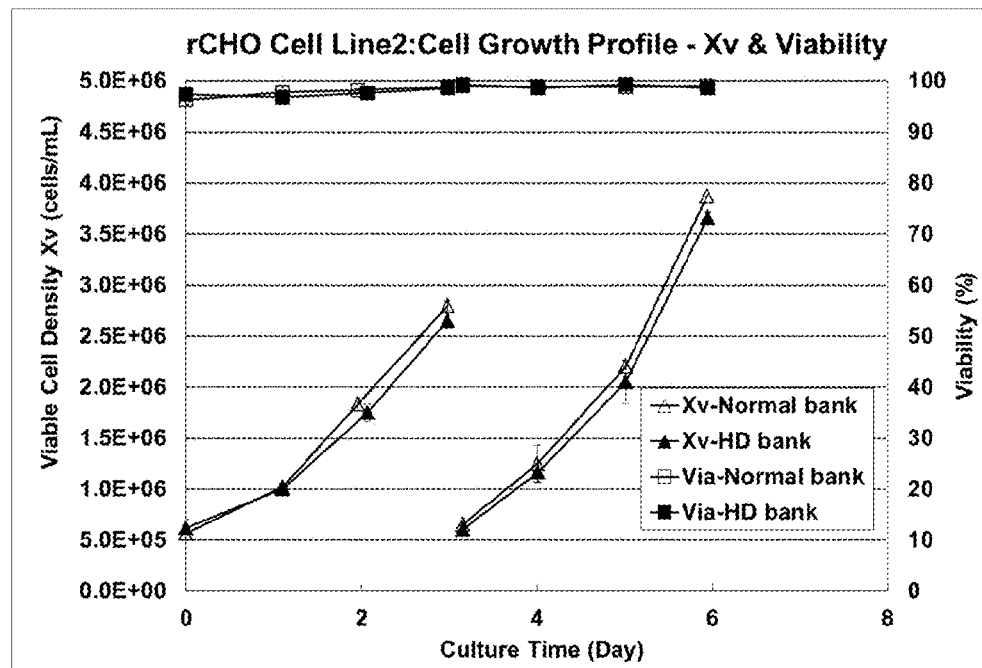
FIG. 9A-B: is a chart of the post-banking performance (A) and late apoptosis (B) of the rCHO cell line 2 high density bank as compared to a normal density bank.
Figure 9:
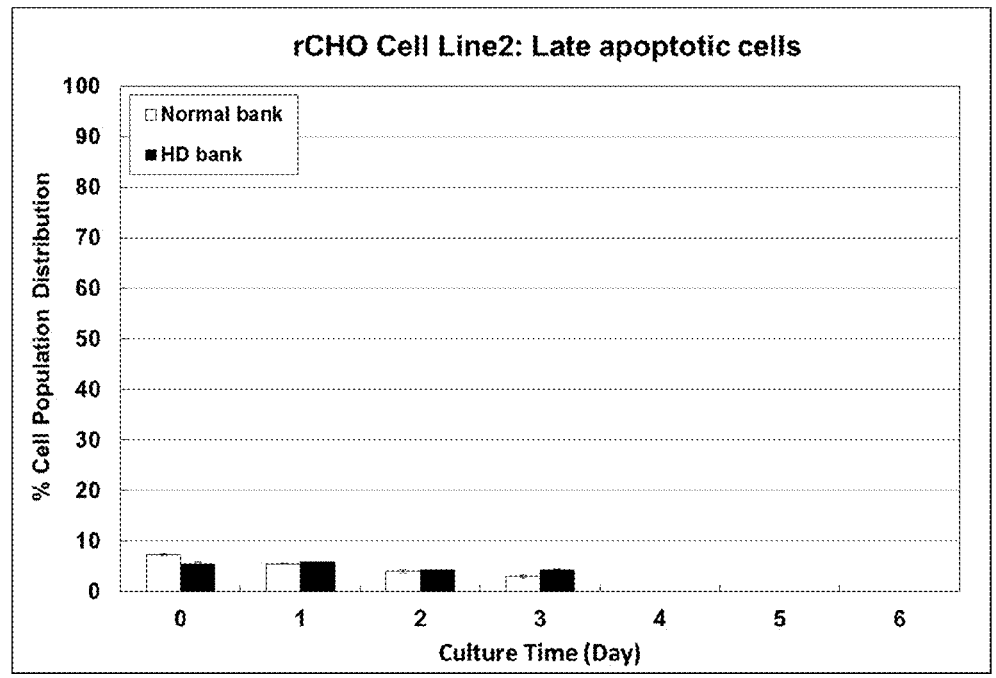
Figure 10:
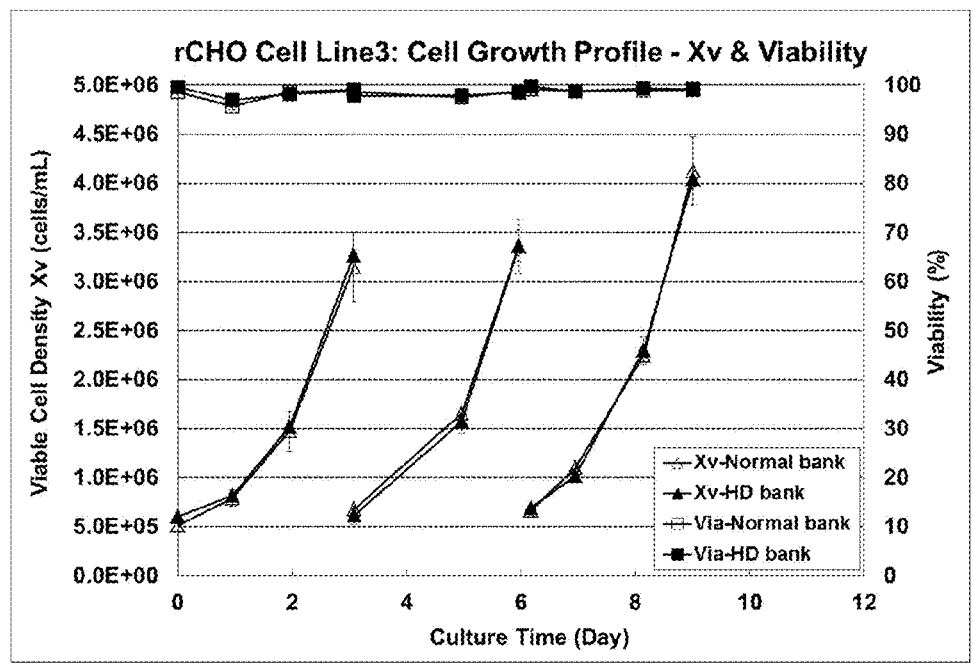
FIG. 10A-B: is a chart of the post-banking performance (A) and late apoptosis (B) of the rCHO cell line 3 high density bank as compared to a normal density bank.
Figure 10:
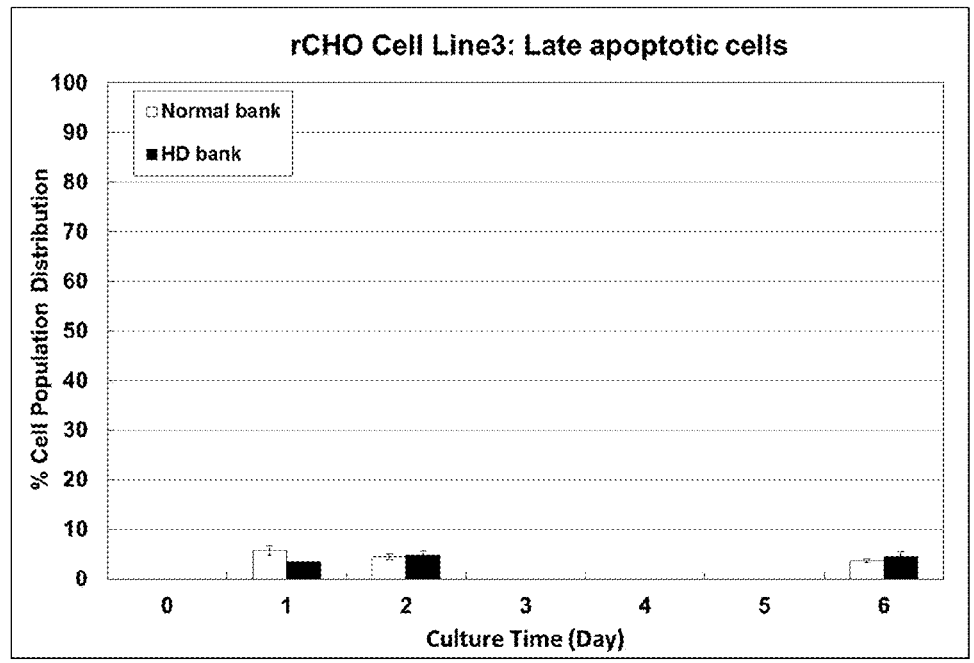

Post-thaw cell growth, viability, and levels of apoptosis were evaluated for rCHO cell line 1 (FIG. 8A-B), rCHO cell line 2 (FIG. 9A-B), and rCHO cell line 3 (FIG. 10A-B) in both high-density (10×10$^7$ cells/mL) and normal-density (2.0-2.4×10$^6$ viable cells/mL) banked samples. The cells showed good growth rates and viability with low levels of apoptosis. Recovery rates varied depending on the cell lines being examined.

We claim:

1. A non-centrifugal method for producing a high-density frozen mammalian cell bank, the method comprising:
   a) culturing mammalian cells in a perfusion bioreactor to a first cell density by continuously removing growth medium from a culture and replacing with fresh growth medium, wherein the bioreactor is coupled to a cell retention system comprising an alternating tangential flow filtration system including a filter;
   b) non-centrifugally concentrating the cells cultured in the perfusion bioreactor coupled to the cell retention system, wherein the cells are concentrated to a second cell density greater than the first cell density by removing the growth medium from the culture using the filter and, thereby reducing the volume of the growth medium to produce a concentrated cell population of about 1×10$^8$ cells/mL; and
   c) cryopreserving the concentrated cell population to produce a high-density frozen mammalian cell bank, wherein the high-density frozen mammalian cell bank has a post-thaw viability of at least 90%.

2. The method of claim 1, wherein the filter has a surface area of at least 0.3 $m^2$.

3. The method of claim 1, wherein the filter has a surface area of about 0.5 to about 1.0 $m^2$.

4. The method of claim 1, wherein the filter has a surface area of about 0.7 to about 0.8 $m^2$.

5. The method of claim 1, wherein the filter has a surface area of about 2.0 to about 3.0 $m^2$.

6. The method of claim 1, wherein the filter has a surface area of about 4 to about 5 $m^2$.

7. The method of claim 1, wherein the filter has a pore size of about 0.2 µm.

8. The method of claim 1, wherein the cryopreserving comprises adding DMSO to the concentrated cell population at a final concentration of about 5% to about 10%, vol/vol.

9. The method of claim 1, wherein the cryopreserving comprises freezing at least a portion of the concentrated cell population in a container for storage under cryopreservation conditions.

10. The method of claim 9, wherein the container is a vial.

11. The method of claim 9, wherein the container has a volume of at least 2 mL.

12. The method of claim 11, wherein the container has a volume of about 5 mL.

13. The method of claim 9, wherein the container is a cryobag.

14. The method of claim 13, wherein the cryobag has a volume of about 5 to about 150 mL.

15. The method of claim 1, wherein the high-density frozen mammalian cell bank comprises about $4.5 \times 10^8$ viable cells.

16. The method of claim 1, wherein the high-density frozen mammalian cell bank has a cell density of about $1 \times 10^8$ viable cells/mL.

17. The method of claim 1, wherein the perfusion rate in the perfusion bioreactor is about 0.2 nL/cell/day.

18. The method of claim 1, wherein the perfusion bioreactor cell culture has a pH of about 7 and a dissolved oxygen concentration of about 40%.

19. The method of claim 1, wherein the perfusion bioreactor is a flexible bag bioreactor.

20. The method of claim 19, wherein the flexible bag bioreactor has a volume of 10 L.

21. The method of claim 19, wherein the flexible bag bioreactor has a volume of at least 20 L.

22. The method of claim 19, wherein the flexible bag bioreactor further comprises at least one dip tube.

23. The method of claim 1, wherein the high-density frozen mammalian cell bank has a post-thaw viability of at least 95%.

24. The method of claim 1, wherein the mammalian cells are selected from the group consisting of: CHO, CHO-DBX11, CHO-DG44, CHO-S, CHO-K1, Vero, BHK, HeLa, COS, MDCK, HEK-293, NIH-3T3, W138, BT483, Hs578T, HTB2, BT20, T47D, NS0, CRL7030, HsS78Bst cells, PER.C6, SP2/0-Ag14, and hybridoma cells.

25. The method of claim 1, wherein the cells are transfected cells.

26. The method of claim 1, wherein the pH and DO of the culture in the perfusion bioreactor are controlled by automated methods.

27. The method of claim 26, wherein the pH and DO of the culture in the perfusion bioreactor are controlled through any one or more of the following: adjustment of the mixture of gases that are introduced to the culture, adjustment of the rock rate of the bioreactor, or adjustment of the rock angle of the bioreactor.

28. The method of claim 1, wherein the pH and DO of the culture in the perfusion bioreactor are controlled by non-automated methods.

29. The method of claim 28, wherein the bioreactor is rocked at 15 rpm with a rock angle of 8°.

30. A non-centrifugal method for producing a high-density frozen mammalian cell bank, the method comprising:
a) culturing mammalian cells in a perfusion bioreactor to a cell density less than $1 \times 10^8$ cells/mL by continuously removing growth medium from a culture and replacing with fresh growth medium, wherein the perfusion bioreactor is coupled to an alternating tangential flow filtration system having a filter, wherein the bioreactor comprises a flexible bag bioreactor, and wherein the filter has a filter surface area of at least 0.3 $m^2$ and a filter with a MWCO size of at least 50 kDa;
b) non-centrifugally concentrating the cells cultured in the perfusion bioreactor coupled to the cell retention system, wherein the cells are concentrated by removing growth medium from the culture and, reducing the volume of the growth medium using the alternating tangential flow filtration system to produce a concentrated cell population having a density of about $1 \times 10^8$ cells/mL;
c) cryopreserving the concentrated cell population to produce a high-density frozen mammalian cell bank, wherein the cryopreserving comprises adding DMSO to the concentrated cell population to a final concentration of about 5% to about 10%, vol/vol; and
wherein the high-density frozen mammalian cell bank has a cell density of about $10^8$ cells/mL; and wherein the high-density frozen mammalian cell bank has a post-thaw viability of at least 90%.

* * * * *